(12) United States Patent
Akimoto et al.

(10) Patent No.: US 7,943,334 B2
(45) Date of Patent: May 17, 2011

(54) METHOD OF DETECTING ALLERGEN

(75) Inventors: Masanobu Akimoto, Tsuchiura (JP);
Shigeki Katou, Tsuchiura (JP); Makoto Namioka, Tsuchiura (JP)

(73) Assignee: Prima Meat Packers, Ltd., Tokyo (JP)

( * ) Notice: Subject to any disclaimer, the term of this patent is extended or adjusted under 35 U.S.C. 154(b) by 867 days.

(21) Appl. No.: 10/591,834

(22) PCT Filed: Mar. 4, 2005

(86) PCT No.: PCT/JP2005/003799
§ 371 (c)(1),
(2), (4) Date: Mar. 15, 2007

(87) PCT Pub. No.: WO2005/085847
PCT Pub. Date: Sep. 15, 2005

(65) Prior Publication Data
US 2007/0275427 A1    Nov. 29, 2007

(30) Foreign Application Priority Data

Mar. 5, 2004 (JP) .................. 2004-063071
Sep. 29, 2004 (JP) .................. 2004-285542
Sep. 29, 2004 (JP) .................. 2004-285543

(51) Int. Cl.
*G01N 33/53* (2006.01)
*G01N 33/543* (2006.01)
*G01N 33/558* (2006.01)
*G01N 33/577* (2006.01)
*C07K 16/02* (2006.01)
*C07K 16/18* (2006.01)

(52) U.S. Cl. ...... 435/7.94; 435/7.1; 435/7.93; 435/7.95; 435/70.21; 435/287.2; 435/287.7; 435/287.9; 436/513; 436/514; 436/518; 436/548; 530/388.2; 530/388.9; 530/391.1; 530/850; 530/868

(58) Field of Classification Search .................. 435/7.1, 435/7.93, 7.94, 7.95, 70.21, 287.2, 287.7, 435/287.9; 436/513, 518, 548, 514; 530/388.2, 530/388.9, 391.1, 850, 868
See application file for complete search history.

(56) References Cited

U.S. PATENT DOCUMENTS

| 4,376,110 | A  | * | 3/1983 | David et al. ............ 435/5 |
| 5,602,040 | A  | * | 2/1997 | May et al. ............ 436/514 |
| 2003/0044869 | A1 | * | 3/2003 | Yeung et al. ............ 435/7.92 |

FOREIGN PATENT DOCUMENTS

| EP | 1 440 978 A1 | | 7/2004 |
| JP | 2002-253230 | * | 9/2002 |
| JP | 2002-253230 A | | 9/2002 |
| JP | 2003-155297 A | | 5/2003 |
| WO | WO-03/022876 A1 | | 3/2003 |

OTHER PUBLICATIONS

Kilshaw et al., 1986. Studies on the specificity of antibodies to ovalbumin in normal human serum: technical considerations in the use of ELISA methods. Clin. Exp. Immunol. 66: 481-489.*
Campbell, 1991. Monoclonal Antibody and Immunosensor Technology, Elsevier, Amsterdam. pp. 3-6 and 45.*
Mine et al., 2002. Comparative studies on antigenicity and allergenicity of native and denatured egg white proteins. J. Agric. Food Chem. 50: 2679-2683.*
Noriko Bando, et al., "Quantitative Analysis of Gly m Bd 28K in Soybean Products by a Sandwich Enzyme-Linked Immunosorbent Assay", Journal Nutritional Science and Vitaminology, vol. 44, No. 5, Oct. 1998, pp. 655-664.
A. Gaiaschi, et al., "Proteolysis of $\alpha_s$-Casein as a Marker of Grana Padano Cheese Ripening", Journal of Dairy Science, vol. 83, No. 12, Dec. 2000, pp. 2733-2739.
Konrad M. Kuzmanoff et al., "Isolation and Characterization of Monoclonal Antibodies Monospecific for Bovine $\alpha$-Casein and $\beta$-Casein", Journal of Dairy Science, vol. 74, No. 3, 1991, pp. 803-810.
Dr. J. M. Wai, "Structure and Function of Milk Allergens", Allergy European Journal of Allergy and Clinical Immunology, Supplement 2001, DK, vol. 56, No. 67, 2001, pp. 35-38.
Supplementary European Search Report dated Mar. 14, 2008, issued in EP 05 72 0071 A1.
International Search Report dated May 31, 2005, issued in PCT/JP2005/003799.

* cited by examiner

*Primary Examiner* — Shafiqul Haq
*Assistant Examiner* — James L Grun
(74) *Attorney, Agent, or Firm* — Venable LLP; Nancy J. Axelrod; Robert Kinberg

(57) ABSTRACT

The present invention provides an immunological detection method that can detect milk allergens, allergens of albumen, flour, buckwheat and peanut with high sensitivity in foods containing these allergens regardless they are denatured/native, and a detection kit to be used therefor. It is a method for detecting allergens by using 2 or more monoclonal antibodies recognizing native and denatured milk allergens, native and denatured albumen allergens, native and denatured flour allergens, native and denatured buckwheat allergens, and native and denatured peanut allergens, using asl casein which is the main protein of milk casein, $\beta$-lactoglobulin which is the main protein of whey, ovalubumin and ovomucoid which are main proteins of albumen, gliadin which is the main protein of flour, protein with a molecular weight of 24 kDa and 76 kDa which are main proteins of buckwheat, and Ara h1 which is the main protein of peanut as an index.

4 Claims, 8 Drawing Sheets

[Fig. 1]
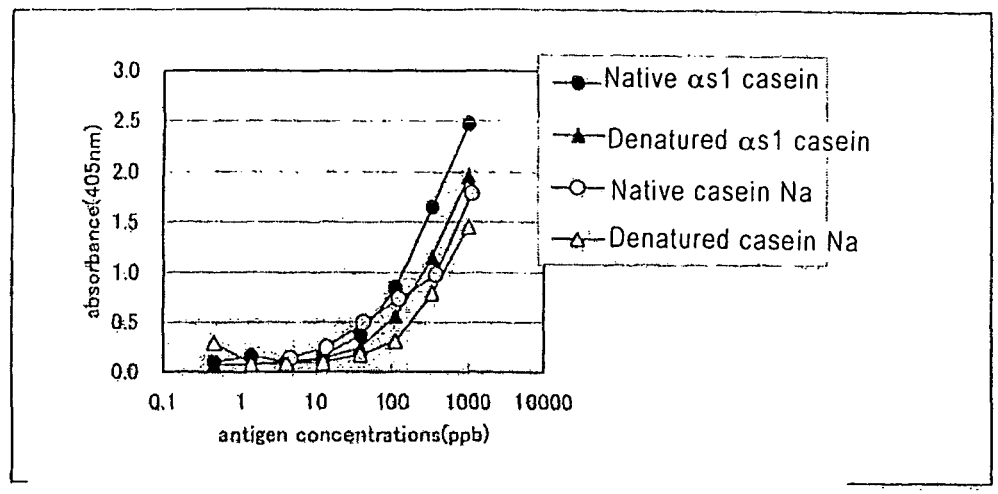
[Fig. 2]
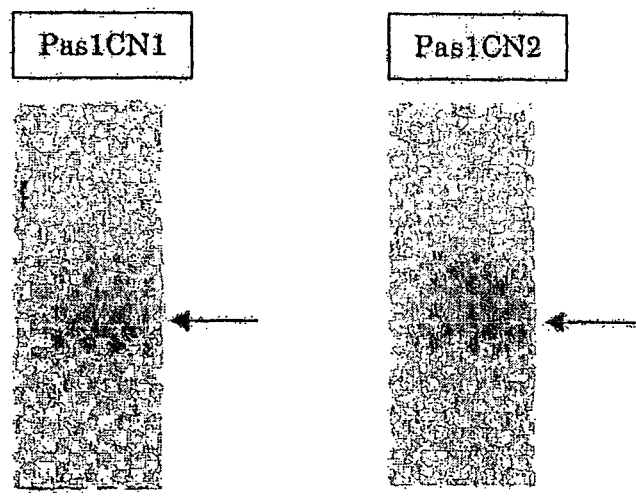
[Fig. 3]
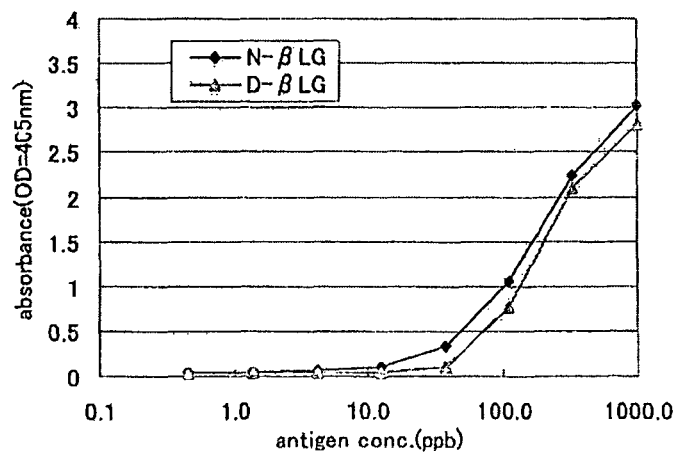

[Fig. 4]
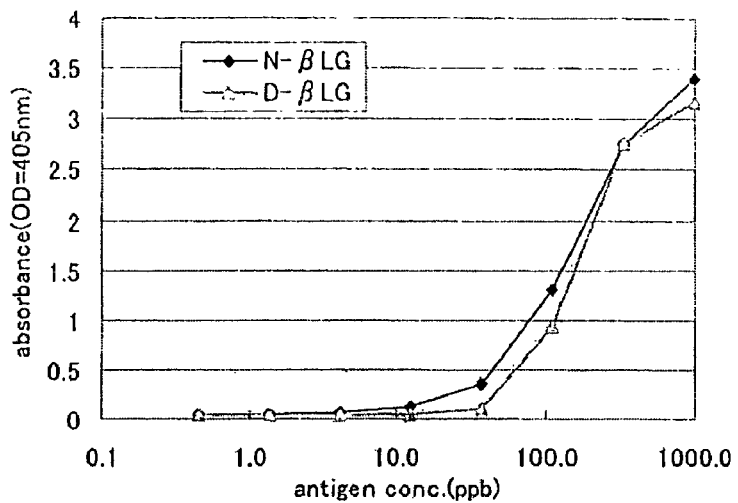
[Fig. 5]
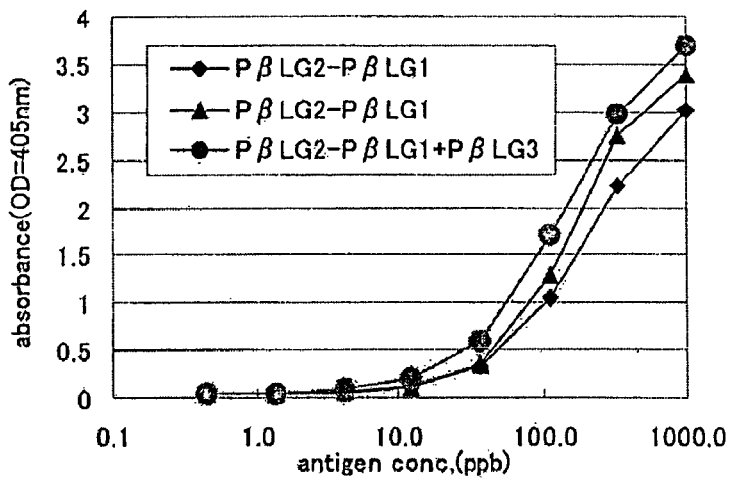
[Fig. 6]
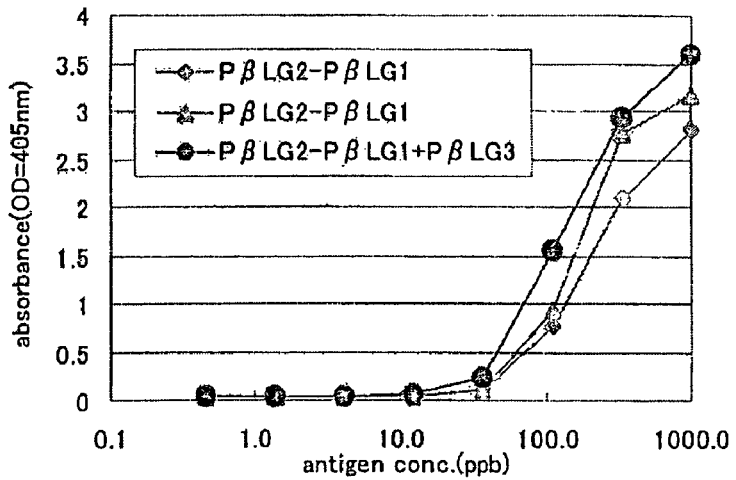

[Fig. 7]
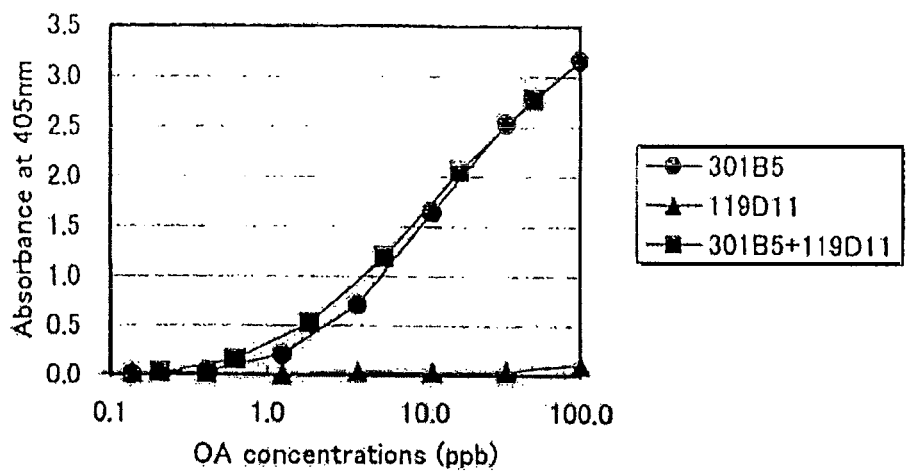
[Fig. 8]
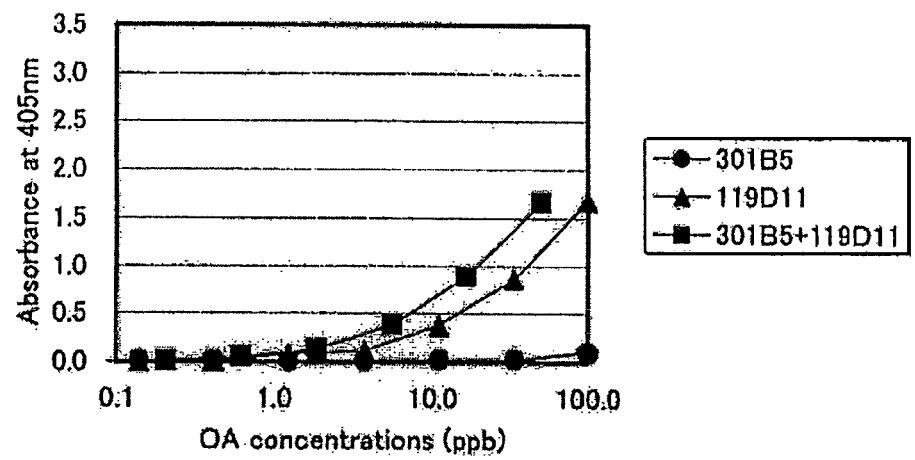
[Fig. 9]
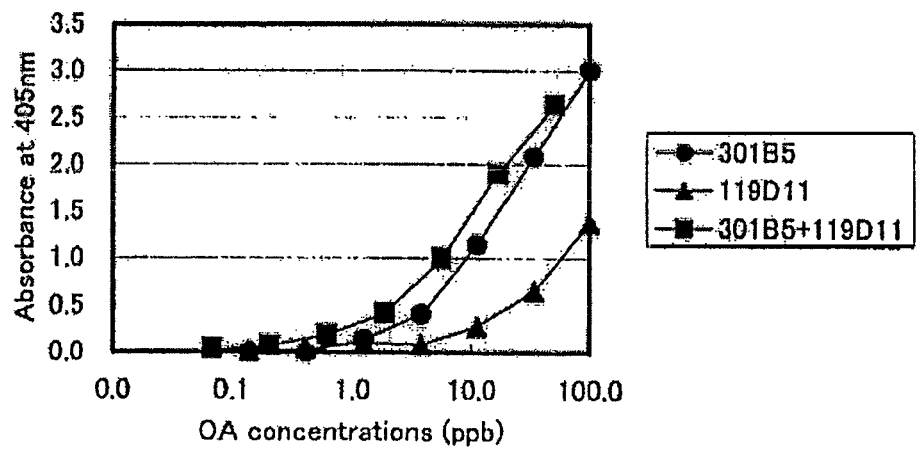

[Fig. 10]
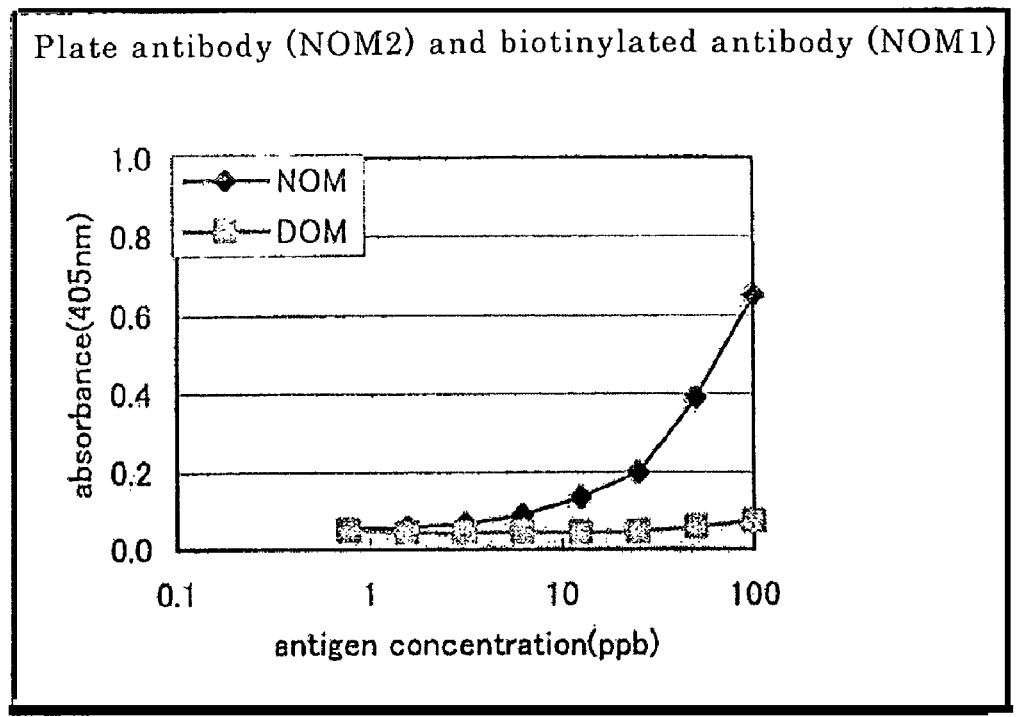
[Fig. 11]
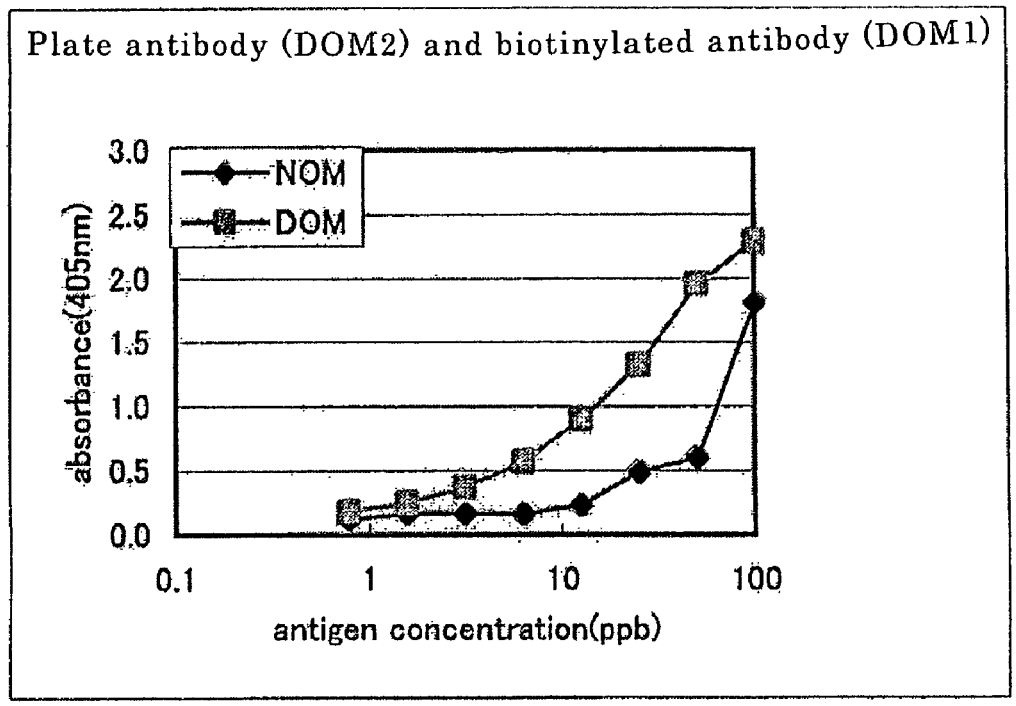

[Fig. 12]
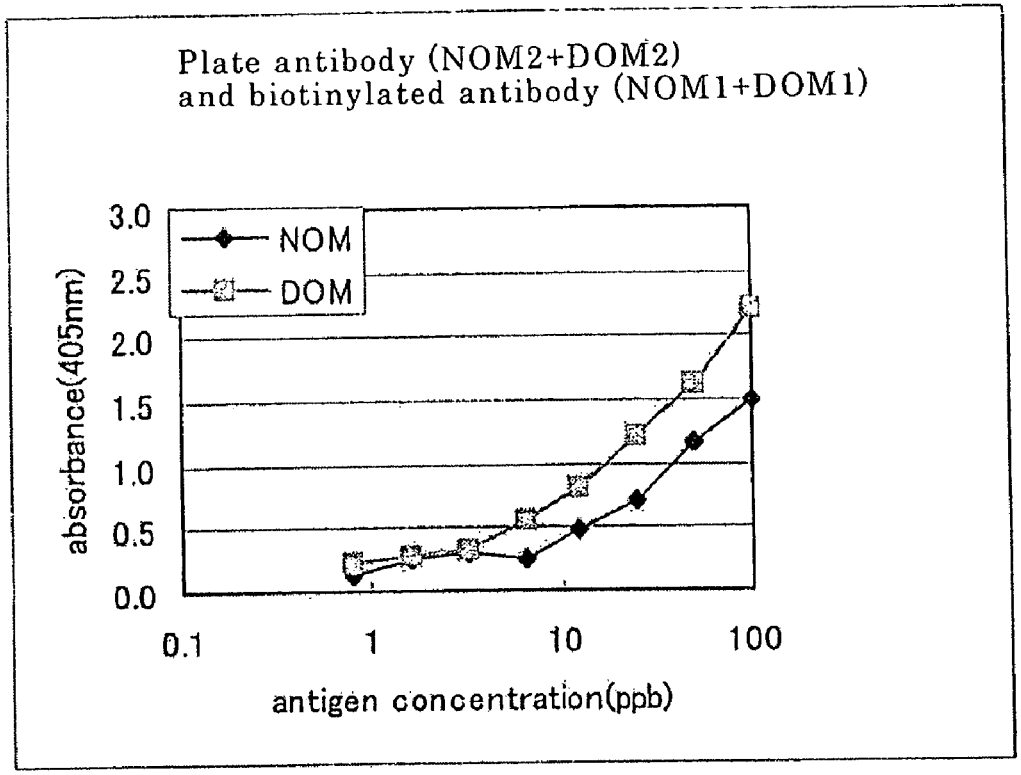
[Fig. 13]
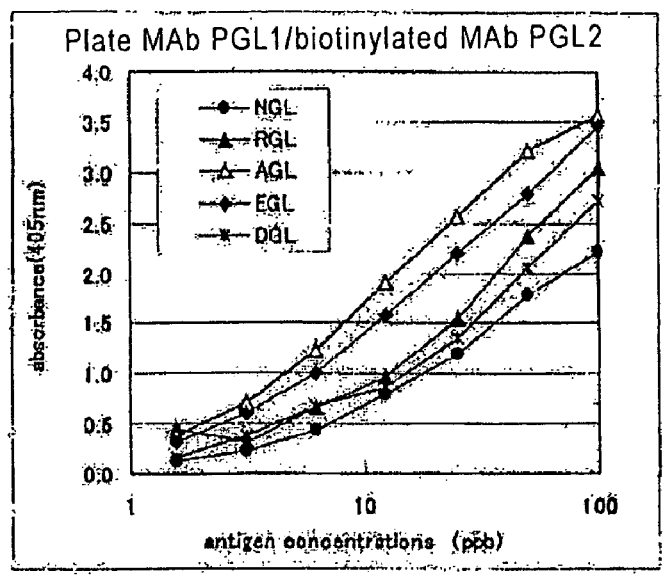

[Fig. 14]
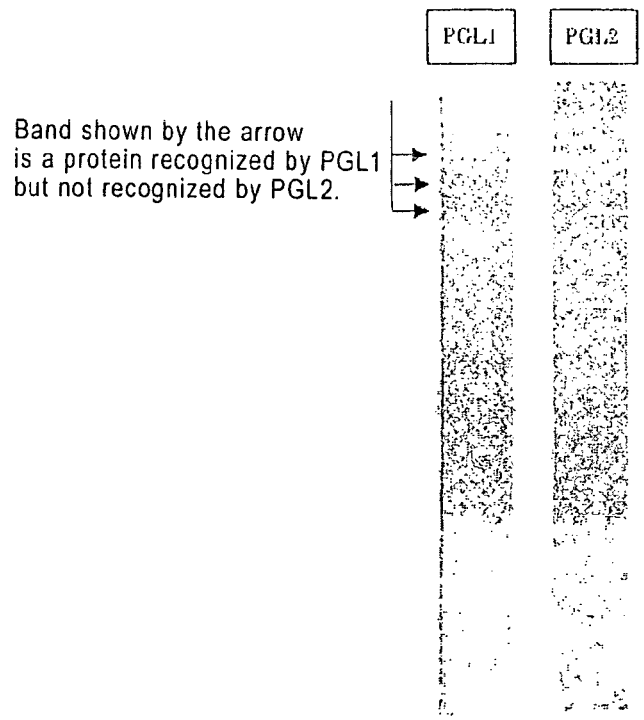
Band shown by the arrow is a protein recognized by PGL1 but not recognized by PGL2.
[Fig. 15]
Combinations of MAb by sandwich ELISA
(plate antibody PBW2-biotinylated antibody PBW3)
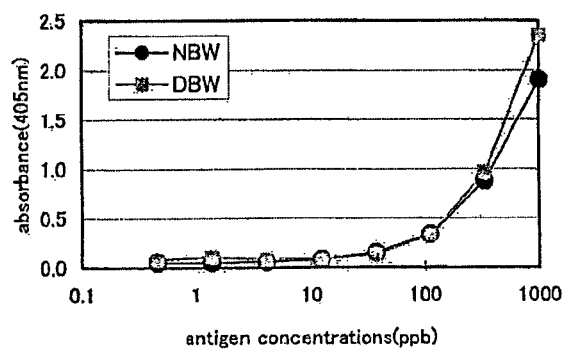
[Fig. 16]
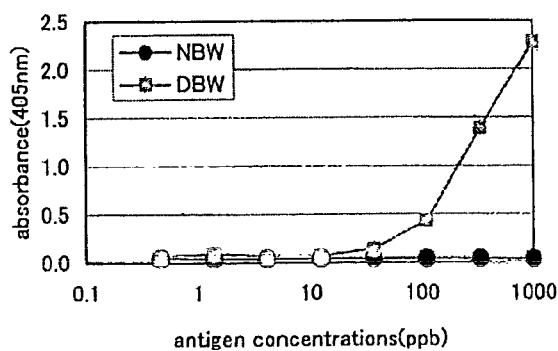

[Fig. 17]
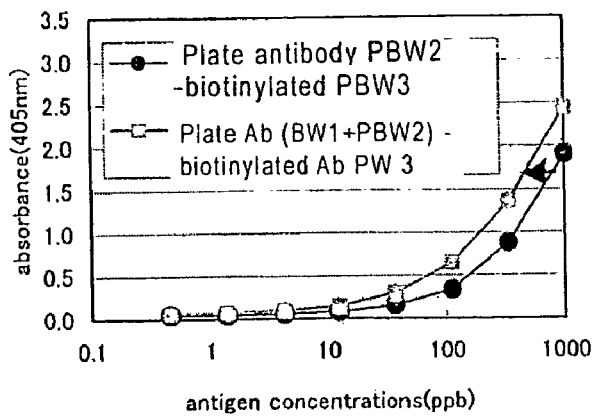
[Fig. 18]
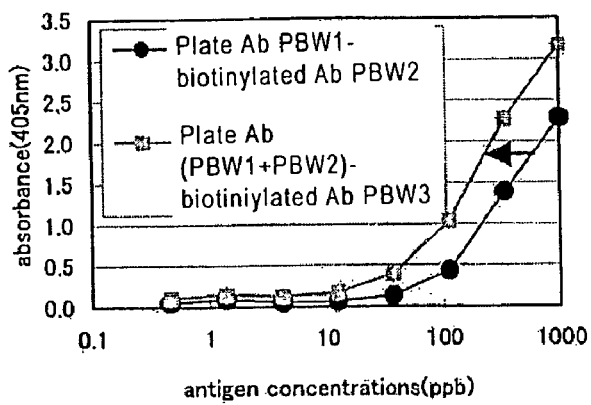
[Fig. 19]
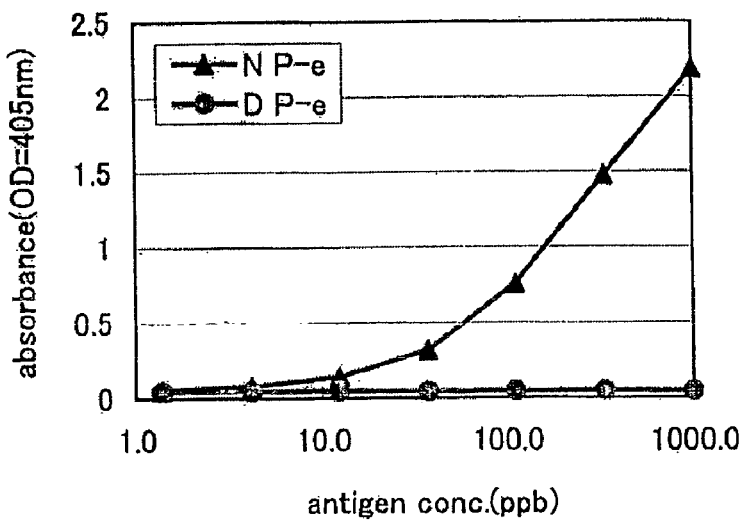

[Fig. 20]
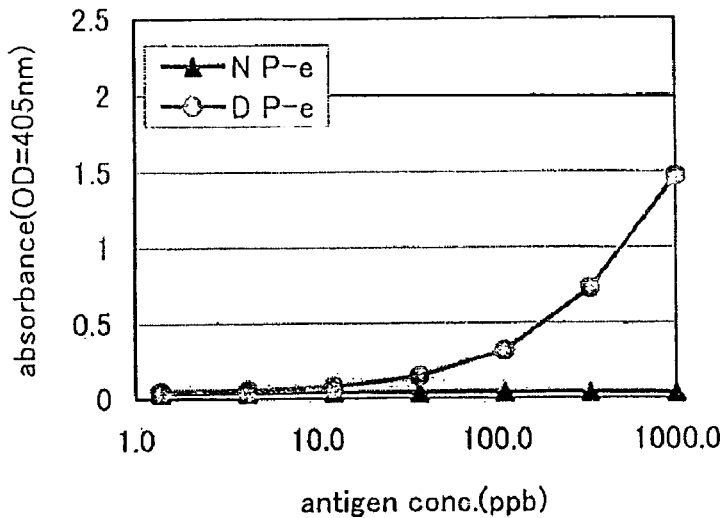
[Fig. 21]
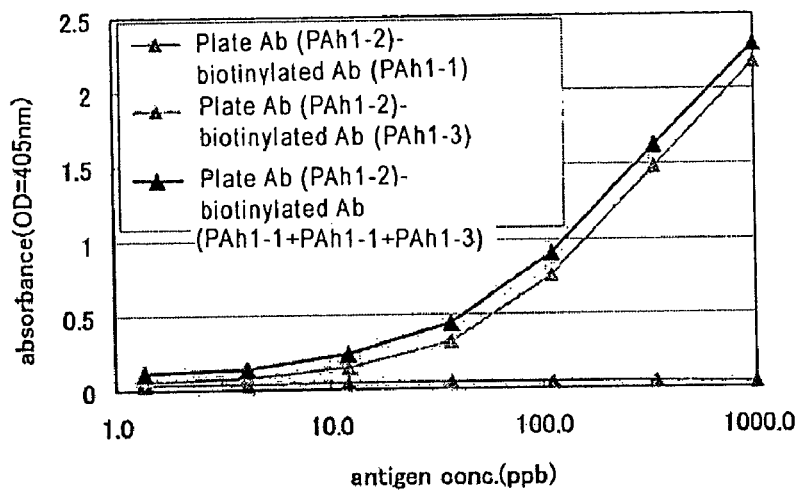
[Fig. 22]
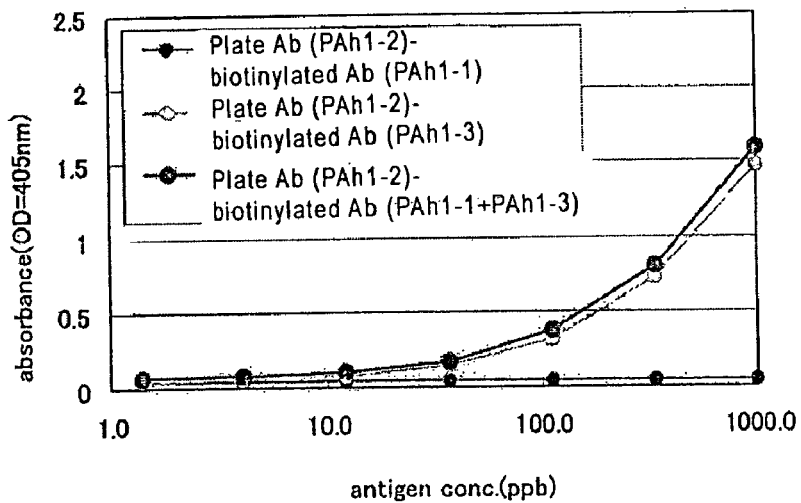

SEQUENCE LISTING

<160> NUMBER OF SEQ ID NOS: 1

<210> SEQ ID NO 1
<211> LENGTH: 199
<212> TYPE: PRT
<213> ORGANISM: cow

<400> SEQUENCE: 1

Arg Pro Lys His Pro Ile Lys His Gln Gly Leu Pro Gln Glu Val Leu
1               5                   10                  15

Asn Glu Asn Leu Leu Arg Phe Phe Val Ala Pro Phe Pro Gln Val Phe
            20                  25                  30

Gly Lys Glu Leu Val Asn Glu Leu Ser Lys Asp Ile Gly Ser Glu Ser
        35                  40                  45

Thr Glu Asp Gln Ala Met Glu Asp Ile Lys Gln Met Glu Ala Glu Ser
    50                  55                  60

Ile Ser Ser Ser Glu Glu Ile Val Pro Asn Ser Val Gln Gln Lys His
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Lys Val Pro Gln Leu Glu Ile Val
            100                 105                 110

```
Pro Asn Ser Ala Glu Glu Arg Leu His Ser Met Lys Glu Gly Ile His
        115                 120                 125

Ala Gln Gln Lys Glu Pro Met Ile Gly Val Asn Gln Glu Leu Ala Tyr
        130                 135                 140

Phe Tyr Pro Glu Leu Phe Arg Gln Phe Thr Gln Leu Asp Ala Tyr Pro
145                 150                 155                 160

Ser Gly Ala Trp Tyr Tyr Val Pro Leu Gly Thr Gln Tyr Thr Asp Ala
                165                 170                 175

Pro Ser Phe Ser Asp Ile Pro Asn Pro Ile Gly Ser Glu Asn Ser Glu
            180                 185                 190

Lys Thr Thr Met Pro Leu Trp
        195
```

METHOD OF DETECTING ALLERGEN

TECHNICAL FIELD

The present invention relates to a method for detecting milk allergens contained in samples such as foods, using native and denatured milk allergens, native and denatured albumen allergens, native and denatured flour allergens, native and denatured buckwheat allergens or native and denatured peanut allergens as an index, and to a kit for detecting milk allergen to be used therefor.

Further, the present invention relates to a method for detecting allergens that can analyze native and denatured milk allergens contained in samples such as foods, qualitatively and quantitatively with high sensitivity using αs1 casein which is the main protein of casein or β-lactoglobulin which is the main protein of whey as an index, and to a kit for detecting allergen to be used therefor.

Moreover, the present invention relates to a method for detecting albumen allergens that can analyze albumen allergen such as native or denatured ovalbumin or ovomucoid contained in samples such as foods, qualitatively or quantitatively with high sensitivity, using ovalbumin and/or ovomucoid as an index, and to a kit for detecting albumen allergens to be used therefor.

Furthermore, the present invention relates to a method for detecting flour allergens that can analyze native and denatured flour allergens contained in samples such as foods, qualitatively or quantitatively with high sensitivity, and using gliadin which is the main protein of flour as an index and to a kit for detecting flour allergens to be used therefor.

Further, the present invention relates to a method for detecting buckwheat allergens that can analyze native and denatured buckwheat allergens contained in samples such as foods, qualitatively or quantitatively with high sensitivity, and using proteins with a molecular weight of 24 kDa and 76 kDa which is main proteins of buckwheat as an index, and to a kit for detecting buckwheat allergens to be used therefor.

Furthermore, the present invention relates to a method for detecting peanut allergens that can analyze native and denatured peanut allergen contained in samples such as foods, qualitatively or quantitatively with high sensitivity, and using Ara h1 which is the main protein of peanut as an index, and to a kit for detecting peanut allergens to be used therefor.

BACKGROUND ART

Due to various factors including degradation of natural environment, gas emission from cars or industrial plants, housing conditions etc., or change of foods, it is said that one out of 3 persons suffers currently from some kind of allergic disease. Especially, food allergy is a harmful immune response induced by an intake of allergy-inducing substances (hereinafter referred to as food allergen) which induces dermatitis, asthma, gastrointestinal impairment, anaphylaxis shock, etc. As the number of patients suffering such food allergy increases, severe problems are arising in the medical field, as well as in food industry. These hazards sometimes lead to death, and it is necessary to take some medical procedures in advance. Thus, necessity to provide information to consumers on a label is increasing, and the Joint FAO/WHO Food Standard Committee has agreed to indicate the content of foods containing 8 types of raw materials known as allergic substances. It was decided that each member country would consider an indication method appropriate to the system of each country (June 1999). In Japan, a labeling method was established for 24 foods, which have actually induced severe allergic symptoms, by taking into account the degree or frequency of health damage in the past (executed from April 2002). Eggs, milks, meats, fishes, shellfishes and mollusks, cereals, beans and nuts, fruits, vegetables, beer yeast, gelatin, etc. are known as foods inducing allergy. Especially, αs1 casein as a main ingredient of milk allergen, β-lactoglobulin as a main ingredient of whey allergen, ovalbumin and ovomucoid as albumen allergens, gliadin as a main ingredient of flour allergen, proteins with a molecular weight of 24 kDa and 78 kDa as main ingredients of buckwheat, or Ara h1 as a main ingredient of peanut are known.

Conventionally, as methods for detecting allergens, for example, a method for quantifying immunoglobulin that reacts specifically to allergens (see Japanese Laid-Open Patent Application No. 05-249111), a method for measuring allergen-specific IgE antibody in a sample comprising dissociating an antigen-antibody complex in the sample by acid treatment and the like, and performing neutralization treatment by using alkali according to need (Japanese Laid-Open Patent Application No. 07-140144), etc. are known.

Further, as official methods (KOTEI-HO; Japan) for detecting specified raw materials such as milk, egg, flour, buckwheat, and peanut, an immunological detection method using polyclonal antibodies obtained from heated/non-heated complex antigens (see Japanese Laid-Open Patent Application No. 2003-155297; hereinafter referred to as "commercial KOTEI-HO A"), or an immunological detection method using polyclonal antibodies obtained from purified antigens (herein after referred to as "commercial KOTEI-HO B") are currently used. These methods are effective for specifically detecting allergens, while they also have many problems. For example, as complex antigens are used in commercial KOTEI-HO A, it is unclear against what the antigen, and the crossing property is high. For example, antigens cannot be identified by immunoblotting, etc. and there is a possibility that non-specific responses increase. On the other hand, in commercial KOTEI-HO B, the specificity of antigens is clear as the antigens have been purified. However, as antibodies prepared by using native antigens are used, the binding-level of antibody is different depending on whether it is native or denatured, which leads to a problem that the quantitative level differs before and after heating, even when the added amount is the same. Especially, as flour is often subjected to severe heating treatment compared to other specified raw materials (eggs, milk, buckwheat, peanut), (for example, bread, fried food, etc.), flour allergens are present in a wide range, from a native state to a denatured state by heating. Therefore, it is necessary to prepare a monoclonal antibody which makes it clear to what stage of allergen the antibody is bound, and to use the antibody according to its property.

Further, for identification and quantitative determination of eggs, a method using a polyclonal antibody using ovomucoid as an index (see for example, Int. Archs. Allergy appl. Immun., 75, 8-15, 1984), or a method using a monoclonal antibody (see for example, Nutr. Sci. Vitaminol. 45, 491-500, 1999) is known. Moreover, an immunological quantitative method has been reported which enables identification and accurate quantitation of egg allergens by determining ovomucoid by discriminating even a denatured state by heating, with the use of a monoclonal antibody which recognizes ovomucoid, wherein the monoclonal antibody reacts with native ovomucoid while not reacting with heat-denatured ovomucoid, or that reacts with heat-denatured ovomucoid while that does not react with native ovomucoid, or that reacts with native ovomucoid and heat-denatured ovomucoid (see for example, Japanese Laid-Open Patent Application No. 2002-253230).

DISCLOSURE OF THE INVENTION

The object of the present invention is to provide an immunological detection method that can detect milk allergens, albumen allergens, flour allergens, buckwheat allergens and peanut allergens in either of native or denatured state with high sensitivity, in foods containing milk allergen, albumen allergen, flour allergen, buckwheat allergen, or peanut allergen, and a detection kit to be used therein, etc.

The present inventors made a keen study on a method for detecting allergens in milk, albumen, flour, buckwheat, or peanut, which are specified raw materials and they found out that by using 2 or more types of monoclonal antibodies recognizing native and denatured milk allergens, native and denatured albumen allergens, native and denatured flour allergens, native and denatured buckwheat allergens, or native and denatured peanut allergens, allergens of each of these specified raw materials can be detected.

In order to investigate a detection method of milk, which is one of the specified raw materials, $\alpha s1$ casein which is the main protein of casein was used as an index to produce monoclonal antibodies (hereinafter sometimes referred to as MAb) thereto, and among these, plural MAbs that can recognize native $\alpha s1$ casein, urea-treated $\alpha s1$ casein, native sodium casein, and denatured sodium casein, were selected. The present inventors found out combinations of MAbs that can qualitatively and quantitatively analyze $\alpha s1$ casein, urea-treated $\alpha s1$ casein, native sodium casein, and denatured sodium casein even at a concentration between 100 to 1000 ppb, by sandwich ELISA. Further, they confirmed that by using these MAbs, a person using a detection method or a detection kit of the present invention could easily detect milk allergens from test target products, regardless of how the milk allergen in food have been processed.

Further, in order to investigate a detection method of milk, which is one of the specified raw materials, β-lactoglobulin which is the main protein of whey was used as an index to produce monoclonal antibodies thereto, and among these, plural MAbs that can recognize native β-lactoglobulin, urea-treated lactoglobulin, reduced carboxymethylated β-lactoglobulin, were selected. The present inventors found out combinations of MAbs that can qualitatively and quantitatively analyze native β-lactoglobulin, urea-treated β-lactoglobulin, reduced carboxymethylated β-lactoglobulin even at a concentration between 30 to 1000 ppb. Further, they confirmed that by using these MAbs, a person using a detection method or a detection kit of the present invention could easily detect milk allergens from test target products, regardless of how the milk allergen in food have been processed.

In order to investigate a detection method of albumen, which is one of the specified raw materials, monoclonal antibodies against purified ovalbumin or ovomucoid were produced, and among these, plural MAbs that can bind to native antigens and plural MAbs that can bind to denatured antigens were selected respectively. The present inventors found out that by combining a native antigen-bound MAb group and a denatured antigen-bound MAb group, ovalbumin or ovomucoid could be detected with a high sensitivity as an antigen, regardless of their condition, denatured or native. Especially, they confirmed that when a native antigen-bound MAb group and a denatured antigen-bound MAb group are used in combination, the detection can be made with a superior sensitivity compared to when a native antigen-bound MAb (group) or the denatured antigen-bound MAb (group) is used independently, even when native ovalbumin or ovomucoid, or denatured ovalbumin or ovomucoid is present alone. Further, they confirmed that by combining MAbs against ovalbumin and ovomucoid which are albumen allergens, a person using a detection method or a detection kit of the present invention could easily detect albumen allergens, regardless of how the albumen allergen in food have been processed.

In order to investigate a detection method of flour, which is one of the specified raw materials, monoclonal antibodies against purified gliadin were produced, and plural MAbs that can recognize native flour gliadin, reduced carboxymethylated flour gliadin, and flour gliadin solubilized with 0.1 M acetate, flour gliadin solubilized with 70% ethanol, flour gliadin solubilized with a denaturant were selected. The present inventors found out combinations of MAbs that can qualitatively and quantitatively analyze native flour gliadin, reduced carboxymethylated flour gliadin, flour gliadin solubilized with 0.1 M acetate, flour gliadin solubilized with 70% ethanol, and flour gliadin solubilized with a denaturant, even at a concentration between 10 to 100 ppb, by sandwich ELISA. Further, they confirmed that by using these MAbs, a person using a detection method or a detection kit of the present invention could easily detect flour allergen from test target products, regardless of how the flour allergen in food have been processed.

In order to investigate a detection method of buckwheat, which is one of the specified raw materials, monoclonal antibodies against purified 24 kDa-protein, or purified 76 kDa-protein were produced, and among these, plural MAbs that can recognize 24 kDa-protein or 76 kDa-protein were selected. The present inventors found out, combinations of MAbs bondable to native buckwheat protein with MAbs bondable to denatured buckwheat protein that can analyze buckwheat proteins with a high sensitivity, regardless of their state, that is whether it is non-heated (native) or heated (denatured) by sandwich ELISA. Further, they confirmed that by using these MAbs, regardless of how the buckwheat allergen in food have been processed, a person using a detection method or a detection kit of the present invention could easily detect buckwheat allergens from test target products.

In order to investigate a detection method of peanut, which is one of the specified raw materials, monoclonal antibodies against purified native Ara h1 (hereinafter sometimes referred to as "NAh1"), or denatured Ara h1 (hereinafter sometimes referred to as "DAh1"), which is a purified Ara h1 that has been denatured with urea and ml2-mercaptoethanol, were produced. Among these, plural MAbs that can recognize NAh1, DAh1, native peanut-crude protein (hereinafter sometimes referred to as "NP-e"), and/or urea-treated peanut-crude protein (hereinafter sometimes referred to as "DP-e") were selected. The present inventors found out, a combination of MAbs that can analyze peanut protein with a high sensitivity regardless of its state, that is whether it is (non-heated) native, or heated (denatured) by sandwich ELISA. Further, they confirmed that by using these MAbs, a person using a detection method or a detection kit of the present invention could easily detect peanut allergen from test target products, regardless of how the peanut allergen in food have been processed.

BRIEF DESCRIPTION OF THE DRAWINGS

[FIG. 1] It is a figure that shows the results of sandwich ELISA to $\alpha s1$ caseins at various states by using 2 types of anti-$\alpha s1$ casein MAbs of the present invention (milk allergen).

[FIG. 2] It is a figure that shows the difference of component protein of flour-$\alpha s1$ casein that is recognized by Pas1CN1 and Pas1CN2 of the present invention (milk allergen).

[FIG. 3] It is a figure that shows the reactivity of PLG2 and PLG1 against various β-lactoglobulins by sandwich ELISA of the present invention (milk allergen).

[FIG. 4] It is a figure that shows the reactivity of PLG2 and PLG3 against various β-lactoglobulins by sandwich ELISA of the present invention (milk allergen).

[FIG. 5] It is a figure that shows the reactivity against native lactoglobulins in a MAb-mixed system by sandwich ELISA of the present invention (milk allergen).

[FIG. 6] It is a figure that shows the reactivity against urea-treated lactoglobulins in a MAb-mixed system by sandwich ELISA of the present invention (milk allergen)

[FIG. 7] It is a figure that shows the reactivity of anti-ovalbumin MAbs against each serial dilution in Test 1 of the present invention (albumen allergen).

[FIG. 8] It is a figure that shows the reactivity of anti-ovalbumin MAbs against each serial dilution in Test 2 of the present invention (albumen allergen).

[FIG. 9] It is a figure that shows the reactivity of anti-ovalbumin MAbs against each serial dilution in Test 3 of the present invention (albumen allergen).

[FIG. 10] It is a figure that shows the reactivity of PNOM1 and PNOM2 against denatured/native ovomucoid by sandwich ELISA of the present invention (albumen allergen).

[FIG. 11] It is a figure that shows the reactivity of PDOM1 and PDOM2 against denatured/native ovomucoid by sandwich ELISA of the present invention (albumen allergen).

[FIG. 12] It is a figure that shows the reactivity of PNOM2 and PDOM2, and PNOM1 and PDOM1 against denatured/native ovomucoid by sandwich ELISA of the present invention (albumen allergen).

[FIG. 13] It is a figure that shows the results of sandwich ELISA against gliadin in various states, using 2 types of anti-gliadin MAbs of the present invention (flour allergen).

[FIG. 14] It is a figure that shows the difference of constitutive protein of flour gliadin recognized by PGL1 and PGL2 of the present invention (flour allergen).

[FIG. 15] It is a figure that shows the reactivity of PBW2 and PBW3 against various buckwheat crude proteins by sandwich ELISA of the present invention (buckwheat allergen).

[FIG. 16] It is a figure that shows the reactivity of PBW1 and PBW2 against various buckwheat crude proteins by sandwich ELISA of the present invention (buckwheat allergen).

[FIG. 17] It is a figure that shows the reactivity of MAb-mixed system of PBW1, PBW2 and PBW3 against native buckwheat crude proteins by sandwich ELISA of the present invention (buckwheat allergen).

[FIG. 18] It is a figure that shows the reactivity of MAb-mixed system of PBW1, PBW2 and PBW3 against denatured buckwheat crude proteins by sandwich ELISA of the present invention (buckwheat allergen).

[FIG. 19] It is a figure that shows the reactivity of PAh1-1 and PAh1-2 against various peanut crude proteins by sandwich ELISA of the present invention (peanut allergen).

[FIG. 20] It is a figure that shows the reactivity of PAh1-2 and PAh1-3 against various peanut crude proteins by sandwich ELISA of the present invention (peanut allergen)

[FIG. 21] It is a figure that shows the reactivity of MAb-mixed system of PAh1-1, PAh1-2 and PAh1-3 against native peanut crude proteins by sandwich ELISA of the present invention (peanut allergen).

[FIG. 22] It is a figure that shows the reactivity of MAb-mixed system of PAh1-1, PAh1-2 and PAh1-3 against denatured peanut crude proteins by sandwich ELISA of the present invention (peanut allergen).

BEST MODE OF CARRYING OUT THE INVENTION

Methods for detecting allergens contained in foods of the present invention are not particularly limited as long as it is a method for detecting allergens by using 2 or more types of monoclonal antibodies recognizing native and denatured milk allergens, native and denatured albumen allergens, native and denatured flour allergens, native and denatured buckwheat allergens, or native and denatured peanut allergens, using αs1 casein which is the main protein of milk casein, β-lactoglobulin which is the main protein of whey, ovalbumin and ovomucoid which are main proteins of albumin, gliadin which is the main protein of flour, proteins with a molecular weight of 24 kDa and 76 kDa which are main-proteins of buckwheat, or Ara h1 which is the main protein of peanut, as an index.

Methods for detecting milk allergens of the present invention are not particularly limited as long as it is an immunological method for detecting milk allergens using monoclonal antibodies recognizing native milk allergens and monoclonal antibodies recognizing denatured milk allergens simultaneously. Further, kits for detecting milk allergens of the present invention are not particularly limited as long as it is an immunological kit for detecting allergens, comprising a monoclonal antibody recognizing native milk allergens and a monoclonal antibody recognizing denatured milk allergens, and used under the condition of using a monoclonal antibody recognizing native milk allergens and a monoclonal antibody recognizing denatured milk allergens are used in combination. However, it is preferable that a kit comprises 2 or more monoclonal antibodies recognizing different epitopes respectively, as monoclonal antibodies recognizing native milk allergens and/or denatured milk allergens. As such monoclonal antibodies recognizing native milk allergens and/or denatured milk allergens, anti-αs1 casein monoclonal antibodies and anti-β-lactoglobulin monoclonal antibodies can be specifically exemplified. "Milk allergens" herein mentioned relates to those comprising αs1 casein which is the main protein of milk casein and/or β-lactoglobulin which is the main protein of whey.

Examples of the above anti-αs1 casein monoclonal antibodies include anti αs1-casein monoclonal antibodies recognizing native αs1 casein, urea-treated αs1 casein, native sodium casein and denatured sodium casein. Specifically, monoclonal antibodies recognizing the 132-193 position of the amino acid sequence of αs1 casein shown by SEQ ID NO: 1 can be preferably exemplified. Specifically, the anti-αs1 casein monoclonal antibody Pas1CN1 produced by hybridoma (FERM ABP-10263), the anti-αs1 casein monoclonal antibody Pas1CN2 produced by hybridoma (FERM ABP-10264) etc. can be preferably exemplified. Moreover, by combining Pas1CN1 and Pas1CN2, sandwich ELISA and immunochromatography can be performed more advantageously. For example, by using these monoclonal antibodies, native αs1 casein and urea-treated αs1 casein in foods can be analyzed qualitatively and quantitatively even at a concentration between 10 to 1000 ppb, by sandwich ELISA.

Examples of the above anti-β-lactoglobulin monoclonal antibody include anti-β-lactoglobulin monoclonal antibodies recognizing native β-lactoglobulin, urea-treated β-lactoglobulin, and reduced carboxymethylated β-lactoglobulin. Specifically, the anti-β-lactoglobulin monoclonal antibody PLG1 produced by hybridoma (FERM ABP-10281) and the anti β-lactoglobulin monoclonal antibody PLG2 produced by hybridoma (FERM ABP-10282), the anti β-lactoglobulin monoclonal antibody PLG3 produced by hybridoma (FERM ABP-10283), etc. can be preferably exemplified. Further, by combining PLG2 and PLG1, PLG2 and PLG3, PLG2, PLG1 and PLG3, sandwich ELISA and immunochromatography can be performed more advantageously. For example, by using these antibodies, native β-lactoglobulin and urea-treated β-lactoglobulin in foods can be analyzed qualitatively and quantitatively even at a concentration between 30 to 1000 ppb, by sandwich ELISA.

In a method for detecting milk allergens of the present invention, it is preferable to extract casein and/or whey protein from a sample by using urea and 2-mercaptoethanol. Moreover, it is preferable to use 1 or more monoclonal antibodies recognizing a native casein and 1 or more monoclonal antibodies recognizing a denatured casein, and 1 or more monoclonal antibodies recognizing a native β-lactoglobulin and 1 or more monoclonal antibodies recognizing a denatured β-lactoglobulin. Moreover, in a kit for detecting milk allergens of the present invention, a kit comprising urea and 2-mercaptoethanol to extract casein and/or whey protein is preferable, and a kit comprising 1 or more monoclonal antibodies recognizing a native casein and 1 or more monoclonal antibodies recognizing a denatured casein, and 1 or more monoclonal antibodies recognizing a native β-lactoglobulin and 1 or more monoclonal antibodies recognizing a denatured β-lactoglobulin, are preferable.

Methods for detecting albumen allergens of the present invention are not particularly limited as long as it is an immunological method for detecting albumen allergens using monoclonal antibodies recognizing native albumen allergens and monoclonal antibodies recognizing denatured albumen allergens simultaneously. Further, kits for detecting albumen allergens of the present invention are not particularly limited as long as it is an immunological kit for detecting allergens, comprising monoclonal antibodies recognizing native albumen allergens and monoclonal antibodies recognizing denatured albumen allergens, and used under a condition where a monoclonal antibody recognizing native albumen allergens and a monoclonal antibody recognizing denatured albumen allergens simultaneously. However, it is preferable to comprise 2 or more monoclonal antibodies recognizing different epitopes respectively, as monoclonal antibodies recognizing native albumen allergens and/or denatured albumen allergens. As such monoclonal antibodies recognizing native albumen allergens and/or denatured albumen allergens, anti-ovalbumin monoclonal antibodies and anti-ovomucoid monoclonal antibodies can be specifically exemplified. "Albumen allergens" herein mentioned relates to those comprising ovalbumin and/or ovomucoid which are main proteins of albumen.

As the above anti-ovalbumin monoclonal antibodies, anti-ovalbumin monoclonal antibodies recognizing a native ovalbumin and/or a reduced carboxymethylated ovalbumin are preferable. Specifically, the anti-ovalbumin monoclonal antibody PNOA1 produced by hybridoma (FERM ABP-10265), the anti-ovalbumin monoclonal antibody PNOA2 produced by hybridoma (FERM ABP-10266), the anti ovalbumin monoclonal antibody PDOA1 produced by hybridoma (FERM ABP-10275), the anti ovalbumin monoclonal antibody PDOA2 produced by hybridoma (FERM ABP-10276) etc. can be preferably exemplified. Further, by using the combination of anti-native ovalbumin monoclonal antibodies such as PNOA1 and PNOA2, and anti denatured ovalbumin monoclonal antibodies such as PDOA1 and PDOA2, or especially by combining anti-native ovalbumin monoclonal antibodies such as PNOA1 and PNOA2 with anti-denatured ovalbumin monoclonal antibodies such as PDOA1 and PDOA2, sandwich ELISA or immunochromatography can be performed more advantageously. For example, by using these antibodies, native ovalbumin and/or denatured ovalbumin in foods can be analyzed qualitatively and quantitatively even at a concentration between 1.0 to 10.0 ppb by sandwich ELISA.

As the above anti-ovomucoid monoclonal antibodies, anti ovomucoid monoclonal antibodies recognizing a native ovomucoid and/or an urea denatured-ovomucoid can be exemplified. Specifically, the anti-ovomucoid monoclonal antibody PNOM1 produced by hybridoma (FERM ABP-10279), the anti-ovomucoid monoclonal antibody PNOM2 produced by hybridoma (FERM ABP-10280), the anti-ovomucoid monoclonal antibody PDOM1 produced by hybridoma (FERM ABP-10277), the anti-ovomucoid monoclonal antibody PDOM2produced by hybridoma (FERM ABP-10278), etc. can be preferably exemplified. Further, by using the combination of anti-native ovomucoid monoclonal antibodies such as PNOM1 and PNOM2, and anti-denatured ovomucoid monoclonal antibodies such as PDOM1 and PDOM2, especially by combining anti-native ovomucoid monoclonal antibodies such as PNOM1 and PNOM2 with anti-denatured ovomucoid monoclonal antibodies such as PDOM1 and PDOM2, sandwich ELISA and immunochromatography can be performed more advantageously. For example, by using these antibodies, native ovomucoid and/or denatured ovomucoid in foods can be analyzed qualitatively and quantitatively even at a concentration between 10 to 100 ppb by sandwich ELISA.

In a method for detecting albumen allergens of the present invention, it is preferable to extract ovalbumin and/or ovomucoid by using urea and 2-mercaptoethanol. Further, it is preferable to use 1 or more monoclonal antibodies recognizing a native ovalbumin and 1 or more monoclonal antibodies recognizing a denatured ovalbumin, and 1 or more monoclonal antibodies recognizing a native ovomucoid and 1 or more monoclonal antibodies recognizing a denatured ovomucoid. Further, for kits for detecting albumen allergens of the present invention, those comprising urea and 2-mercaptomethanol for extracting ovalbumin and/or ovomucoid are preferable, and those comprising 1 or more monoclonal antibodies recognizing a native ovalbumin and 1 or more monoclonal antibodies recognizing a denatured ovalbumin, and 1 or more monoclonal antibodies recognizing a native ovomucoid and 1 or more monoclonal antibodies recognizing a denatured ovomucoid are preferable.

Methods for detecting flour allergens of the present invention are not particularly limited as long as it is an immunological method for detecting flour allergens by using anti-flour gliadin monoclonal antibodies recognizing native a flour gliadin and a flour gliadin solubilized with a denaturant; or an immunological method for detecting flour allergen using in combination 2 types of anti-flour gliadin monoclonal antibodies recognizing a native flour gliadin and a flour gliadin solubilized with a denaturant, and recognizing different epitopes. Further, kits for detecting flour allergens of the present invention are not particularly limited as long as it is an immunological kit for detecting allergens comprising anti-flour gliadin monoclonal antibodies recognizing a native flour gliadin and a flour gliadin solubilized with a denaturant, or an immunological kit for detecting allergen comprising 2 types of anti flour gliadin monoclonal antibodies recognizing a native flour gliadin and a flour gliadin solubilized with a denaturant, and recognizing different epitopes. As the above anti-flour gliadin monoclonal antibodies, anti-flour gliadin monoclonal antibodies recognizing a native flour gliadin, a reduced carboxymethylated flour gliadin, a flour gliadin solubilized with 0.1 M acetate, a flour gliadin solubilized with 70% ethanol, and a flour gliadin solubilized with a denaturant are preferable. Specifically, the anti-flour gliadin antibody PGL1 produced by hybridoma (FERM ABP-10267) and the anti-flour gliadin antibody PGL2 produced by hybridoma (FERM ABP-10268) can be preferably exemplified. By combining these antibodies, sandwich ELISA or immunochromatography can be performed more advantageously. For example, it is possible to analyze qualitatively and quantitatively native flour gliadin, reduced-carboxymethylated flour gliadin, flour gliadin solubilized with 0.1 M acetate, flour gliadin solubilized with 70% ethanol, and flour gliadin solubilized with a denaturant in foods, even at a concentration between 10 to 100 ppb.

Methods for detecting buckwheat allergens of the present invention are not particularly limited as long as it is an immunological method for detecting buckwheat allergens using anti-buckwheat crude protein monoclonal antibodies recognizing a native buckwheat crude protein and a heat-denatured buckwheat crude protein; or an immunological method for detecting buckwheat allergens using 2 types of anti-buckwheat crude protein monoclonal antibodies recognizing a native buckwheat crude protein and a heat-denatured buckwheat crude protein, and recognizing different epitopes. Further, kits for detecting buckwheat allergens of the present invention are not particularly limited as long as it is an immunological kit for detecting allergens comprising anti-buckwheat crude protein monoclonal antibodies recognizing a native buckwheat crude protein and a heat-denatured buckwheat crude protein, or an immunological kit for detecting allergens comprising 2 types of anti-buckwheat crude protein antibodies recognizing a native buckwheat crude protein and a heat-denatured buckwheat crude protein, and recognizing different epitopes. As anti-buckwheat crude protein monoclonal antibodies, anti-buckwheat crude protein monoclonal antibodies recognizing a 24 kDa-protein and a heat-denatured buckwheat crude protein, or anti-buckwheat crude protein monoclonal antibodies recognizing a 76 kDa-protein and a native buckwheat crude protein are preferable. Specifically, the anti-24 kDa protein monoclonal antibody PBW1 produced by hybridoma (FERM ABP-10272), the anti-76 kDa-protein monoclonal antibody PBW2 produced by hybridoma (FERM ABP-10273), the anti-76 kDa protein monoclonal antibody PBW3 produced by hybridoma (FERM ABP-10274) can be preferably exemplified. Further, the combination of anti-buckwheat crude protein monoclonal antibodies recognizing a 24 kDa-protein such as PBW1 and heat-denatured buckwheat crude proteins with anti-buckwheat crude protein monoclonal antibodies recognizing a 76 kDa-protein such as PBW2 and native buckwheat crude proteins; or the combination of anti-buckwheat crude protein monoclonal antibodies recognizing a native buckwheat crude protein such as PBW2 and PBW 3, and a heat-denatured buckwheat crude protein can be preferably exemplified. Further, by combining these antibodies as a mixed system, sandwich ELISA and immunochromatography can be performed more advantageously. For example, native buckwheat crude proteins and heat-denatured crude proteins can be analyzed qualitatively and quantitatively even at a concentration between 10 to 1000 ppb by sandwich ELISA.

Further, in a method of detecting buckwheat allergens of the present invention, it is preferable to extract heat-denatured buckwheat crude proteins by using urea and 2-mercaptoethanol from a sample. Further, as kits for detecting buckwheat allergens of the present invention, those comprising urea and 2-mercaptoethanol as an agent for extracting buckwheat crude proteins from a sample are preferable.

Methods for detecting peanut allergens of the present invention are not particularly limited as long as it is an immunological method for detecting peanut allergens using anti-Ara h1 protein monoclonal antibodies recognizing a native peanut Ara h1 protein and a heat-denatured peanut Ara h1 protein, or an immunological method for detecting peanut allergens using 2 types of anti-Ara h1 protein monoclonal antibodies recognizing a native peanut Ara h1 protein and a heat-denatured peanut Ara h1 protein, and recognizing different epitopes. Further, kits for detecting peanut allergens of the present invention are not particularly limited as long as it is an immunological kit for detecting allergens comprising anti-peanut Ara h1 protein monoclonal antibodies recognizing a native peanut Ara h1 protein and a heat-denatured peanut Ara h1 protein, or an immunological kit for detecting allergens comprising 2 types of anti-peanut Ara h1 protein monoclonal antibodies recognizing a native peanut Ara h1 protein and a heat-denatured peanut Ara h1 protein, and recognizing different epitopes. As anti-Ara h1 protein monoclonal antibodies, anti-Ara h1 protein monoclonal antibodies recognizing a native Ara h1 protein and a native peanut crude proteins and/or urea-treated Ara h1 proteins and urea-treated peanut crude proteins are preferable. Specifically, the anti-native Ara h1 protein monoclonal antibody PAh1-1 produced by hybridoma (FERM ABP-10269), the anti-native Ara h1 protein monoclonal antibody PAh1-2 produced by hybridoma (FERM ABP-10270), the anti-heat-denatured Ara h1 protein monoclonal antibody PAh1-3 produced by hybridoma (FERM ABP-10271) can be preferably exemplified. Further, by using the combination of anti-Ara h1 protein monoclonal antibodies recognizing native a Ara h1 protein such as PAh1-1 and a denatured peanut crude proteins, and anti-Ara h1 protein monoclonal antibodies recognizing a native/denatured Ara h1 protein such as PAh1-2 and a native/denatured peanut crude proteins, or the combination of anti-Ara h1 protein monoclonal antibodies each recognizing a native/denatured Ara h1 protein such as PAh1-2 and PAh1-3, and a native/denatured peanut crude protein, and further by combining these antibodies as a mixed system, sandwich ELISA and immunochromatography can be performed more advantageously. For example, native peanut Ara h1 proteins and heat-denatured peanut Ara h1 proteins can be analyzed qualitatively and quantitatively even at a concentration between 10 to 1000 ppb, by sandwich ELISA.

Moreover, in a method for detecting peanut allergens of the present invention, it is preferable to extract heat-denatured peanut crude protein from a sample by using urea and 2-mercaptoethanol. Further, as kits for detecting peanut allergens of the present invention, those comprising urea and 2-mercaptoethanol as agents for extracting heat-denatured peanut crude proteins from a sample are preferable.

The above immunological methods for detecting allergen of the present invention comprise the following steps: an immune reaction step wherein a sample comprising native/denatured milk allergens, native/denatured albumen allergens, native/denatured flour allergens, native/denatured buckwheat allergens or native/denatured peanut allergens (hereinafter sometimes referred to as "food allergens") is allowed to contact a labeled anti-food allergen MAb, or to contact a food allergen MAb in the presence of a labeled antibody, and to trap as a labeled immune complex by an antigen-antibody reaction; and a detection step wherein the generated immune complex is separated/measured by using labeled substances which are present in the molecule. Methods of antigen-antibody reaction in the immune response step are not particularly limited, and the following can be exemplified.

The examples include: a sandwich method wherein a food allergen in a sample is trapped to an anti-food allergen MAb of the present invention bound to an in solubilized carrier, and then allowed to react a labeled anti-IgG antibody; a double-antibody sandwich method using a labeled anti-food allergen MAb (secondary antibody) recognizing an epitope different from an anti-food allergen MAb bound to an in solubilized carrier; a competitive method wherein a food allergen in a sample is allowed to react with an anti-food allergen MAb bound to an insolubilzed carrier in the presence of a labeled antigen; a magnetic bead method wherein a magnetic bead-bound labeled anti food allergen MAb reacting specifically with a sample containing a food allergen is allowed to react with the sample, and then a labeled substance in an immune complex separated magnetically is detected; an agglutination-precipitation method wherein a labeled anti-food allergen MAb reacting specifically with a sample containing a food allergen is allowed to react with the sample, and to agglutinate and precipitate, and then a labeled substance in an immune complex separated by centrifugation is detected; an immunochromatology method wherein an anti-food allergic protein MAb binding to a food allergen is fixed in advance on the test strip where an antigen-antibody complex, in which an anti-food allergen MAb labeled with such as gold colloid and a food allergenic protein are bound, moves by a capillary phenomenon etc., and a qualitative analyze is performed according to the presence or absence of a colored line appearing by trapping the antigen-antibody complex. Besides these examples, known immunoassays including a double immunodiffusion method or a radio immunodiffusion method can be used. However, a method using 2 or more monoclonal antibodies recognizing different epitopes, as food allergen antibodies, for example a double-antibody sandwich method that can analyze qualitatively and quantitatively native allergens and/or denatured allergens even at a concentration between 100 to 1000 ppb, is preferable for its high sensitivity, or an immunochromatography method is preferable qualitatively from the point of its easiness. Further, when extracting allergen from a food sample such as meat products, it is preferable to use urea and 2-mercaptoethanol.

As in solubilized carriers used in the above antigen-antibody reactions, polymers including polystyrene, polyethylene, polypropylene, polyester, polyacrylonitrile, fluorine resin, crosslinking dextran, polysaccharide, as well as glass, metal, magnetic particles and combinations thereof can be exemplified. The form of in solubilized carriers can be for example, a form of tray, sphere, fiber, bar, disk, container, cell, microplate, test tube or latex bead, and various forms can be used. Further, methods for fixing antigens or antibodies to these in solubilized carriers are not particularly limited, and physical absorption method, covalent binding method, ion binding method and the like can be used.

Classes and types of immune globulin of anti-food allergen MAbs used in a method for detecting food allergens or in a kit for detecting food allergens of the present invention are not particularly limited, while antibodies of IgG class or type κ are preferably used as anti-food allergen MAbs. Further, as configuration of monoclonal antibodies, a full antibody, and fragments including F (ab')$_2$, or Fab can be used. Origins of antibodies are not particularly limited, and examples include mouse, rat, human, rabbit and chicken. However, monoclonal antibodies derived from a mouse are preferably used as it is easy to prepare. Further, anti-food allergen MAbs can be prepared by culturing hybridomas prepared by cell fusion of antibody-producing cells collected from animals immunized with native or denatured αs1 casein and myeloma cells in a medium, or by administering the hybridomas in an animal intraperitoneally and proliferating the same, and then collecting from the culture or the ascetic fluid.

Anti-food allergen MAb-producing hybridomas can be produced by, for example, immunizing a BALB/c mouse by using native and/or denatured food allergens, performing cell fusion of antibody-producing cells of the immunized mouse and mouse myeloma cells by common methods, and screening by immunofluorescent staining patterns. The above antibody-producing cells include, for example, spleen cells, lymph node cells and B-lymphocytes obtained from immunized animals that have been administered with native and/or denatured food allergens or a composition containing the same. As animals to immunize, mice, rats, rabbits and horses can be exemplified. Immunization is performed by, for example, administering native and/or food allergens directly or with an appropriate adjuvant to an animal, subcutaneously, intramuscularly or intraperitoneally, 1 or 2 times per month, for 1 to6 months. Separation of antibody-producing cells is performed by collecting from the immunized animals, 2 to 4 days after the final immunization. As myeloma cells, those derived from mice or rats can be used. It is preferable that antibody-producing cells and myeloma cells are from the animals of the same species.

Cell fusion can be performed by mixing antibody-producing cells and myeloma cells in a medium such as Dulbecco's modified Eagle medium (DMEM), in the presence of fusion promoters such as polyethylene glycol. After the cell fusion, hybridomas are selected by diluting appropriately with DMEM etc., centrifuging, and suspending the precipitates in a selective medium such as HAT medium, and culturing the same. Subsequently, antibody-producing hybridomas are searched by enzymatic-antibody method with the use of a culture supernatant, cloned by a limiting dilution method, etc. to obtain hybridomas producing anti-food allergen MAbs. Further, anti-denatured food allergen MAbs can also be obtained advantageously from anti-immunized animals immunized with only native food allergens such as αs1 casein. In that case, anti-denatured food allergen MAb-producing hybridomas such as anti-denatured αs1 casein MAbs can be screened; or monoclonal antibody-producing hybridomas against native food allergens such as native αs1 casein can be selected by ELISA at a solid-phase condition, to obtain anti-food allergen MAbs which only react specifically to native food allergens in liquid-phase condition from the monoclonal antibodies generated from the antibody-producing hybridomas. As described above, monoclonal antibodies can be collected from cultures after culturing antibody-producing hybridomas in a medium or in vivo. Methods for separating/purifying monoclonal antibodies from the cultures or the ascetic fluid are not particularly limited as long as it is a method generally used for protein purification. For example, it can be performed by ammonium sulfate fractionation method generally used for IgG purification, or by chromatography by anion exchange, or columns such as protein A and G.

Labeled substances used for labeled antibody preparation are not particularly limited as long as it is a labeled substance that can induce a signal which can be detected alone or by reacting with other substances. Enzymes, fluorescent substances, chemical photosubstances, radioactive substances and gold colloids can be used. Enzymes include peroxidase, alkaline phosphatase, β-D-galactosidase, glucose oxydase, glucose-6-phophate dehydrogenase, alcohol dehydrogenase, malate dehydrogenase, penicillinase, catalase, apoglucose oxidase, urease, luciferase or acetyl cholinesterase. Fluorescent substances include fluorescein isothiocyanate, phycobiliprotein, rare-earth metal chilate, dansylchloride or tetramethylrodamine isothiocyanate. Photosubstances include luminols, dioxetanes, acridinium salts. Radioactive substances include $^3$H, $^{14}$C, $^{125}$I or $^{131}$I. When a labeled substance is an enzyme, substrates can be used to measure its activity as well as coloring agents, fluorescent agents, radio agents, according to need.

Kits for measuring food allergens of the present invention comprises anti-food allergen MAbs as active ingredients, preferably 2 or more types of anti-food allergen MAbs recognizing different epitopes, which are stored preferably as a lyophilizate than in a fluid condition, from the point of view of storage stability. Kits for detection may comprise buffer solution and the like for preparing a sample, besides buffer solution or culture solution to solubilize anti-food allergen MAbs. Further, as a more preferable embodiment of a kit for detecting anti-food allergens of the present invention, test strips of the above immunochromatography can be exemplified. In that case, at least one of the 2 types of monoclonal antibodies recognizing different epitopes is preferably a monoclonal antibody labeled with gold colloid used in the immunochromatography.

Monoclonal antibodies of the present invention include: anti-αs1 casein monoclonal antibody Pas1CN1 generated by hybridoma (FERM BP-10263); anti-αs1 casein monoclonal antibody Pas1CN2 generated by hybridoma (FERM BP-10264); anti-β-lactoglobulin monoclonal antibody PLG1 generated by hybridoma (FERM BP-10281); anti-β-lactoglobulin monoclonal antibody PLG2 generated by hybridoma (FERM BP-10282); anti-β-lactoglobulin monoclonal antibody PLG3 generated by hybridoma (FERM BP-10382); anti-ovalbumin monoclonal antibody PNOA1 generated by hybridoma (FERM BP-10265); anti-ovalbumin monoclonal antibody PNOA2 generated by hybridoma (FERM BP-10266); anti-ovalbumin monoclonal antibody PDOA1 generated by hybridoma (FERM BP-10275); anti-ovalbumin monoclonal antibody PDOA2 generated by hybridoma (FERM BP-10276); anti-ovomucoid monoclonal antibody PNOM1 generated by hybridoma (FERM BP-10279); anti-ovomucoid monoclonal antibody PNOM2 generated by hybridoma (FERM BP-10280); anti-ovomucoid monoclonal antibody PDOM1 generated by hybridoma (FERM BP-10277); anti-ovomucoid monoclonal antibody PDOM2 generated by hybridoma (FERM BP-10278); anti-flour gliadin monoclonal antibody PGL1 generated by hybridoma (FERM BP-10267); anti-flour gliadin monoclonal antibody PGL2 generated by hybridoma (FERM BP-10268); anti-24 kDa protein monoclonal antibody PBW1 generated by hybridoma (FERM BP-10272); anti-76 kDa protein monoclonal antibody PBW2 generated by hybridoma (FERM BP-10273); anti-76 kDa protein monoclonal antibody PBW3 generated by hybridoma (FERM BP-10274); anti-native Ara h1 protein monoclonal antibody PAh1-1 generated by hybridoma (FERM BP-10269); anti-native Ara h1 protein monoclonal antibody PAh1-2 generated by hybridoma (FERM BP-10270); and anti-heat-denatured Ara h1 protein monoclonal antibody PAh1-3 generated by hybridoma (FERM BP-10271). These hybridomas have been accepted at National Institute of Advanced Industrial Science and Technology, International Patent Organism Depository (Central 6, 1-1, Higashi 1-chome Tsukuba-shi, Ibaraki-ken 305-5466, Japan) on Feb. 24, 2005 (date of receipt). Meanwhile, the above-mentioned Pas1 CN1 (FERM P-20206), Pas1CN2 (FERM P-20207), PNOA1 (FERM P-20208), PNOA2 (FERM P-20209, PGL1 (FERM P-20210), PGL2 (FERM P-20211) are those deposited at National Institute of Advanced Industrial Science and Technology, International Patent Organism Depository, on Sep. 7, 2004 (date of deposit).

In the following, the present invention is explained in more detail by referring to the Examples, while the technical scope of the present invention is not limited to these exemplifications.

EXAMPLE 1

1. Establishment of Anti-αs1 Casein Monoclonal Antibodies
1-1 Materials and Methods
1) Preparation of αs1 Casein (Hereinafter Referred to as "αCN")

Crude fractions of αCN were obtained from fresh milk, according to Zittle (1959). The crude fractions were further purified by using TSK gel DEAE 650S (TOSOH) with a linear gradient (0 to 0.3 M) of NaCl containing 50 mM of imidazole-HCl buffer solution (pH 6.4) and 4M of urea. The purified αCN fraction was dialyzed with distilled water and then lyophilized. A 0.1% solution of the lyophilizates was prepared with saline, which was aliquoted in 1 ml-volume Eppendorf tubes at 500 µl per tube, stored by freezing at −20° C. until immunization, and the resultant was used as an antigen solution.

2) Immunization

As test animals, 5 BALB/c mice (CLEA Japan) of 6 weeks-old were used. For the primary immunization, an emulsion, prepared by adding a complete Freund's adjuvant (Difco) to an Eppendorf tube filled with 500 µl of 0.1% αCN at an equal amount, and stirring in a vortex mixer, was used. The emulsion was injected intraperitoneally in an amount of 150 µl per mouse. Further, additional immunizations were performed twice at 3 weeks interval. For immunization, an emulsion prepared by adding an incomplete Freund's adjuvant (Difco) to each Eppendorf tube filled with 500 µl of 0.1% αCN at an equal amount, and stirring in a vortex mixer was used. The emulsion was injected intraperitoneally in an amount of 150 µl per mouse.

3) Measurement of Antibody Titer in Blood

One week after injecting αCN as the primary or additional immunization, blood was collected from tail vein of each BALB/c mouse. The blood collected was allowed to stand for 2 hours at room temperature, and centrifuged to obtain serum. 10-fold serial dilution of these sera was prepared, and the anti-αCN antibody titer in the mouse blood was examined by non-competitive ELISA. Meanwhile, alkaline phosphatase labeled-anti mouse IgG (H+L) antibodies (Jackson ImmunoResearch Laboratories Inc.) were used as secondary antibodies.

2) Preparation of Hybridomas

Hybridomas were prepared according to the methods of Keller and Milstein (1975). In other words, 100 µl of 0.1% αCN solution was injected into tail vein of a mouse whose antibody titer has sufficiently increased. Spleen was extracted axenically from the mouse 4 days after the intravenous injection. The spleen was chopped, subsequently washed with RPMI 1640, allowed to pass through a sterilized nylon mesh (Cell Strainer, 70 mm, Becton Dickinson), to obtain a spleen cell suspension. Spleen cells were harvested by a centrifugation at 1,000 rpm×10 min, and the cells were counted after resuspending in RPMI 1640. The spleen cell suspension and mouse myeloma cells (P3X63Ag8.653) were mixed such that the cell count becomes 10:1, and then centrifuged again at 1,000 rpm×10 min to obtain a pellet. 45% polyethylene glycol with a mean molecular weight of 3,350 was dropped to the pellet to allow a cell fusion. RPMI 1640 was added to the cell solution, which was diluted. A pellet was obtained by centrifugation. A HAT selective medium consisting of a hybridoma medium (RPMI1640 medium containing 10% bovine fetal serum, 40 mM of 2-mercaptoethanol, 100 U/ml of penicillin, 100 mg/ml of streptomycin) and 100 μM of hypoxanthine, 0.4 μM of aminopterin and 16 μM of thymidine was added the palette. The resultant was aliquoted in 24-well cell culture plate (Becton Dickinson) to $5 \times 10^6$ cells/well, and was cultured at 37° C., in the presence of 5% $CO_2$.

5) Cloning by Limiting Dilution

Presence of hybridomas provided as primary antibodies for ELISA and producing anti-αCN antibodies was examined for the culture supernatant of each well of cell culture plate. Hybridomas which tested positive against αCN by ELISA were transferred to a 96-well cell culture plate (Becton Dickinson) and cloned by limiting dilution to 0.9 cell/well. Meanwhile, as feeder cells, thymocytes of 4-weeks old BALB/c mouse were added to each well of the 96-well cell culture plate, to $5 \times 10^6$ cells/well. RPMI 1640 media containing 10% of bovine fetal serum, 40 mM 2-mercaptoethanol, 100 U/ml of penicillin, 100 μg/ml of streptomycin were used for culturing cloned hybridomas.

6) Screening of Antibodies

By screening monoclonal antibodies, clones having different specificities were obtained by examining the difference of reactivity against 4 types of proteins, that is, native αCN (hereinafter referred to as "N-αCN") urea-treated αCN (hereinafter referred to as "D-αCN"), commercial native substances of sodium casein (hereinafter referred to as "N-CN"), and commercial urea-treated substances of sodium casein (hereinafter referred to as "D-CN"). D-αCN was denatured by the following steps: 1 mg of purified αCN was measured, 100 μl of 5% EDTA, 6.0 g of urea, 0.2 ml 2-mercaptoethanol, 1 ml 50 mM tris-hydrochloric buffer solution (pH 8.6), 1.5 ml distilled water were added to the αCN. The resultant was covered with an aluminum cap, and heated at 100° C. for 1 hour in an oil bath. The reactivity against N-αCN, D-αCN, N-CN or D-CN of the culture supernatant was examined by non-competitive ELISA.

7) Collection of Ascitic Fluid and Purification of MAbs

According to Jones et al. (1990), 0.2 ml of incomplete Freund's adjuvant was injected to a BALB/c mouse intraperitoneally. One week after, $5 \times 10^6$ cells/well of cloned hybridomas were inoculated per mouse. After accumulation of ascitic fluid, the fluid was collected with a syringe. The collected ascitic fluid was purified by Protein G column (Amersham pharmacia).

8) Classes, Subclasses and Types of MAbs

Classes and subclasses of MAbs were determined according to Monoclonal mouse immuno αCN obulin isotyping kit (Pharmingen) as IgG1, IgG2a, IgG2b, IgG3, IgM, IgA, IgL (κ) and IgL (γ).

9) Biotinylation of MAbs

Purified MAbs were biotinylated to be provided to sandwich ELISA. The biotinylated MAb was added with 10 μl of NHS-biotin solution which was prepared with 50 mM of carbonate buffer solution (pH 8.5) to 20 mg/ml and dissolved in DMSO at 3 mg/100 μl. The mixture was stirred and then allowed to stand for 2 hours by icing. Subsequently, it was replaced with PBS to 20 mg/ml.

1-2 Results

1) Selection of MAbs 6 types of MAbs recognizing specifically αs1 casein (αCN) which is a main allergen of milk were obtained. The specificity of these 6 types of MAbs against each antigen, N-αCN, D-αCN, N-CN or D-CN which has been solid-phased was examined by direct ELISA. Further, classes and subclasses of these MAbs were investigated as well. The results are shown in Table 1. In Table 1, "+" represents that MAbs are positive against each solid-phased antigen, and "−" represents that MAbs are negative. As it is shown in Table 1, Pas1CN1, Pas1CN2, Pas1CN3 which are MAbs binding to antigens in every state were selected.

TABLE 1

| MAbs | N-αCN | D-αCN | N-CN | D-CN | Classes, subclasses and Types |
|---|---|---|---|---|---|
| Pas1CN1 | + | + | + | + | IgG1 (κ) |
| Pas1CN2 | + | + | + | + | IgG1 (κ) |
| Pas1CN3 | + | + | + | + | IgG1 (κ) |
| Pas1CN4 | + | − | + | − | IgG1 (κ) |
| Pas1CN5 | + | − | + | − | IgG1 (κ) |
| Pas1CN6 | + | − | + | − | IgG1 (κ) |

2) Combination Conditions in Sandwich ELISA

By using Pas1CN1, Pas1CN2 and Pas1CN3 selected by direct ELISA, sandwich ELISA was performed for all the combinations of MAbs. Combinations of MAbs to detect αCN or CN were selected by sandwich ELISA by using Pas1 CN1, Pas1CN2, Pas1CN3 as a solid-phased or a biotinylated antibody, respectively. As a result, the combination of Pas1CN1 (FERM ABP-10263) and Pas1CN2 (FERM ABP-10264) was selected as a combination enabling detection of N-αCN, D-αCN, N-CN and D-CN. The results are shown in FIG. 1.

2. Epitopes Recognized by Pas1CN1 and Pas1CN2

αs1 casein solution was degraded with lysyl endoprotease and the degradation products were separated by trycin SDS-PAGE (separation gel 16.5%, concentration gel 5%). By using the separated gel, the resultant was transcribed to a PVDF membrane by electro blotting. After allowing the culture supernatant of Pas1 CN1 and Pas1CN2 (1/1000) to react to the transcribed PVDF membrane, the recognized epitopes were confirmed by coloring. The results are shown in FIG. 2. As a result, recognition sites of both Pas1CN1 and PasCN2 was the 132-193 position of the amino acid sequence of αs1 casein shown by SEQ ID NO: 1, with a molecular weight of about 7000.

3. Detection of Native and Denatured Casein in Foods by ELISA

It was investigated whether casein in actual foods could be detected by using the combination of Pas1CN1 and Pas1CN2 selected in the above 1.

3-1 Materials and Methods

1) Preparation of Meat Product Models

Meat products were selected as food models for a quantitative test, and meat product models containing sodium casein at each concentration were prepared in a composition shown in Table 2. Fats and muscles were removed from pork loin meat, and minced to 5 mm, and the resultant was used as lean hog.

TABLE 2

Composition list of meat product models

| Raw material | TEST 1 | TEST 2 | TEST 3 | Control |
|---|---|---|---|---|
| Lean hog (%) | 83.0 | 83.0 | 83.0 | 83.0 |
| NaCl (%) | 2.0 | 2.0 | 2.0 | 2.0 |
| Sodium polyphosphate (%) | 0.2 | 0.2 | 0.2 | 0.2 |
| Sodium nitrite (ppm) | 120 | 120 | 120 | 120 |
| Sodium ascorbate (ppm) | 300 | 300 | 300 | 300 |
| water | 14.5 | 14.5 | 14.5 | 14.5 |
| Sodium casein (ppm) | 200 | 20 | 2 | 0 |
| Total (%) | 99.762 | 99.744 | 99.7422 | 99.742 |

According to each composition, additives were measured, and mixed with a food processor, filled into a vinyl chloride tube, which was heated at 75° C. for 30 min.

2) Quantitative Analysis by Sandwich ELISA

Each meat product model was ground until being homogenized with a food processor, and used as a sample for analysis. 2 g of sample was measured and taken, 38 g of PBST containing 1 M of urea and 0.1% of 2-mercaptoethanol was added, and the resultant was heat treated at 100° C. for 1 hour. After cooling, centrifugation was performed at 3,000 rpm for 20 min, and 9.5 ml of PBST was added to 0.5 ml of supernatant and the resultant was used as a sample for ELISA. Serial dilution of sodium casein treated similarly with urea and 2-mercaptoethanol was used for a standard curve. Further, comparison was carried out with the case where urea and 2-mercaptoethanol were not used and using sodium casein as a standard curve which was extracted from a sample for analysis by using PBST, and dissolved in PBST (PBS added with 0.5% polyoxyethylene sorbitan monolaurate).

3-2 Results

The results of sandwich ELISA by using urea and 2-mercaptoethanol for analysis of sodium casein in food product models are shown in Table 3, and the results of extracting sodium casein with only PBST are shown in Table 4.

TABLE 3

|  | TEST 1 | TEST 2 | TEST 3 | Control |
|---|---|---|---|---|
| Added amount (ppm) | 200.0 | 20.0 | 2.0 | 0.0 |
| Assay value (ppm) | 235.4 | 16.4 | 1.5 | N.D. *2 |
| Yield (%) *1 | 117.7 | 82.0 | 75.0 | — |

*1: (assay value/added amount) × 100
*2: not detected

TABLE 4

|  | TEST 1 | TEST 2 | TEST 3 | Control |
|---|---|---|---|---|
| Added amount (ppm) | 200.0 | 20.0 | 2.0 | 0.0 |
| Assay value (ppm) | 16.1 | 1.7 | N.D. *2 | N.D. |
| Yield (%) *1 | 8.1 | 8.5 | — | — |

*1: (assay value/added amount) × 100
*1: not detected

From the above results, when urea and 2-mercaptoethanol are added to the extraction solution, sodium casein in meat product models can be detected at a high yield, while it showed a significant low yield in PBST extraction. From these results, it was revealed that it is effective to use urea and 2-mercaptoethanol for extracting sodium casein from foods, and for the characteristics of MAbs used therein, it is necessary that the MAbs are bondable to urea-solubilized casein.

4. Detection of Denatured and Native Sodium Casein by Immunochromatography 4-1 Materials and Methods 1) Preparation of Gold Colloid Labels and Conjugate Pads MAb solution of Pas1CN1 was prepared to 1 mg/ml with 2 mM of borate buffer solution (pH 9.0). 500 µl of MAb solution was added to 5 ml of gold colloid solution (Sigma) which was previously prepared to pH 9.0 with 0.2 M carbonic potassium solution, and after allowing to react at room temperature for 30 min, 625 µl of 10% BSA solution was added and was further allowed to react for 15 min. Centrifugation was performed and it was prepared to OD525=1.0 with 1% BSA solution. The resultant was applied to a glass wool conjugate pad to 68 µl/cm², and dried.

2) Preparation of Antibody Fixed Membranes

MAb solution of Pas1CN2 was prepared to 4 mg/ml with PBS, applied linearly on a nitrocellulose membrane and dried. Then, the resultant was blocked for 2 hours, at 37° C., with PBS containing 1% BSA and 0.1% Tween 20.

3) Construction and Estimation of Immunochromato Strips

A sample pad, a conjugate pad, an antibody-fixed membrane and an absorption pad prepared in the above were applied respectively, to make an immunochromato strip. Meat product models prepared in the above were diluted appropriately and used as a test solution.

4-2 Results

By using the combination of Pas1CN2 and gold colloid labeled-Pas1CN1, sodium casein could be detected heated or non-heated, up to 50 ppb (2 ppm in food). From this result, it was revealed that immunochromato stip that can respond to any case could be constructed, even when native sodium casein which had been mixed during the manufacture process was the target, or when a product after heating was the target.

When PBS containing only 0.01 M of urea as a blank was dropped to a commercial immunochromato strip for detecting allergens, a non-specific band appeared, and it was determined as false positive. Thus, a protein denaturant to detect effectively allergens from food protein which was denatured by heating and the like, could not be used, and there was a possible risk that subjects detectable as allergens would be limited to a very narrow range.

5. Establishment of Anti-β-Lactoglobulin Monoclonal Antibodies 5-1 Materials and Methods 1) Preparation of β-Lactoglobulin (Hereinafter Sometimes Referred to as "βLG")

Crude fractions of whey were obtained from fresh milk, according to Zittle (1959). The crude fraction was further purified by using TSK gel DEAE 650S (TOSOH) with a linear gradient (0 to 0.4M) of NaCl, and 50 mM of tris-HCl buffer solution (pH 6.5). The purified βLG fraction was dialyzed with distilled water and then lyophilized, to make a native βLG (hereinafter sometimes referred to as "N-βLG"). 10 mg of the N-βLG was measured, 1 ml of 1.4 M tris-HCl buffer solution (pH8.6), 100 µl of 5% of EDTA, 1.2 g of urea, 33 µl of 2-mercaptoethanol were added to the N-βLG to make a constant volume of 2.5 ml, and a nitrogen gas substitution was performed. Then, the resultant was substituted to reduction treatment at 37° C. for 1 hour, and 89 mg of monoiodoacetic acid dissolved into 300 µl of 1M NaOH was added to perform a nitrogen gas substitution. Subsequently, carboxymethylation was performed at room temperature for 1 hour, to make a reduced carboxymethylated βLG (hereinafter sometimes referred to as "R-βLG"). A 0.1% solution of the lyophilizates was prepared with saline which was aliquoted in 1 ml-volume Eppendorf tubes at 500 µl per tube, and stored by freezing at −20° C. until immunization, and was used as an antigen solution.

2) Immunization

As test animals, 5 BALB-c mice (CLEA Japan) of 5 weeks-old were used. For the primary immunization, an emulsion prepared by adding a complete Freund's adjuvant (Difco) to an Eppendorf tube filled with 500 µl of 0.1% N-βLG or R-βLG, and stirring in a vortex mixer was used. The emulsion was injected intraperitoneally in an amount of 150 µl per mouse. Further, additional immunizations were performed 3 times at 2 weeks interval. For immunization, an emulsion prepared by adding an incomplete Freund's adjuvant (Difco) to each Eppendorf tube filled with 500 µl of 0.1% N-βLG or R-βLG at an equal amount, and stirring in a vortex mixer was used. The emulsion was injected intraperitoneally in an amount of 150 μl per mouse.

3) Measurement of Antibody Titer in Blood

One week after injecting N-βLG or R-βLG as a first or additional immunization, blood was collected from tail vein of each BALB/c mouse. The blood collected was allowed to stand for 2 hours at room temperature, centrifuged to obtain serum. 10-fold dilution of these sera was prepared, and the anti-N-βLG antibody titer and anti-R-βLG antibody titer in mouse blood was examined by non-competitive ELISA. Meanwhile, alkaline phosphatase labeled-anti mouse IgG (H+L) antibody (Jackson ImmunoResearch Laboratories Inc.) was used.

4) Preparation of Hybridomas

Hybridomas were prepared according to the methods of Keller and Milstein (1975). In other words, 100 μl of 0.1% N-βLG solution or R-βLG solution was injected into tail vein of a mouse whose antibody titer has sufficiently increased. Spleen was extracted axenically from the mouse 4 days after intravenous injection. The spleen was chopped, subsequently washed with RPMI 1640, allowed to pass through a sterilized nilon mesh (Cell Strainer, 70 mm, Becton Dickinson), to obtain a spleen cell suspension. Spleen cells were harvested by centrifugation at 1,000 rpm×10 min, and the cells were counted after resuspending in RPMI 1640. The spleen cell suspension and mouse myeloma cells (P3X63Ag8.653) were mixed such that the cell count becomes 10:1, then centrifuged again at 1,000 rpm×10 min to obtain a pellet. 45% polyethylene glycol with a mean molecular weight of 3,350 was dropped to the pellet to allow a cell fusion. RPMI 1640 was added to the cell solution, and the mixture was diluted, centrifuged to obtain a pellet. A HAT selective medium consisting of a hybridoma medium (RPMI1640 medium containing 10% bovine fetal serum, 40 mM of 2-mercaptoethanol, 100 U/ml of penicillin, 100 mg/ml of streptomycin) and 100 μM of hypoxanthine, 0.4 μM of aminopterin and 16 μM of thymidine was added to the pellet. The resultant was aliquoted in 24-well cell culture plate (Becton Dickinson) to 5×10$^6$ cells/well, and was cultured at 37° C., in the presence of 5% $CO_2$.

5) Cloning by Limiting Dilution

Presence of hybridomas provided as primary antibodies of ELISA and producing anti-N-βLG antibody or anti-R-βLG antibody was examined for the culture supernatant of each well of cell culture plate. Hybridomas which tested positive against αCN by ELISA were transferred to a 96-well cell culture plate (Becton Dickinson) and cloned by limiting dilution to 0.9 cell/well. Meanwhile, as feeder cells, thymocytes of 4-weeks old BALB/c mouse were added to each well of the 96-well cell culture plate, to 5×10$^6$ cells/well. RPMI 1640 media containing 10% of bovine fetal serum, 40 mM of 2-mercaptoethanol, 100 U/ml of penicillin, 100 μg/ml of streptomycin were used for culturing cloned hybridomas.

6) Screening of Antibodies

To screen monoclonal antibodies, clones of different specificities were obtained by examining the difference of reactivity against 3 types of protein, N-βLG, R-βLG and urea-treated βLG (hereinafter referred to as "D-βLG"). D-βLG was denatured by the following steps: 1 mg of purified N-βLG was measured, 6.0 g of urea, 0.2 ml of 2-mercaptoethanol, 1 ml of 50 mM tris-hydrochloric buffer solution (pH 8.6), 1.5 ml of distilled water were added. The resultant was covered with an aluminum cap, and heated at 100° C. for 1 hour in an oil bath. The reactivity against N-BLG, R-BLG, or D-BLG of the culture supernatant was examined by non-competitive ELISA.

7) Collecting Ascitic Fluid and Purification of MAb

According to Jones et al. (1990), 0.2 ml of incomplete Freund's adjuvant was injected to a BALB/c mouse intraperitoneally. One week after, 5×10$^6$ cells/well of cloned hybridomas per mouse were inoculated. After accumulation of ascitic fluid, the fluid was collected with a syringe. The collected ascitic fluid was purified by Protein G column (Amersham pharmacia).

8) Classes, Subclasses and Types of MAbs

Solid-phase method was used to determine the characteristics of anti-N-βLGMAb or anti-R-βLGMAb. As solid-phase method, a method comprising the steps of fixing previously N-βLG, R-βLG or D-βLG in wells of cell culture plate and allowing anti-N-βLGMAb or anti-R-βLGMAb react to these fixed antigens, was used. Classes and subclasses of MAbs were determined according to Monoclonal mouse immuno αCN obulin isotyping kit (Pharmingen) as IgG1, IgG2a, IgG2b, IgG3, IgM, IgA, IgL (κ) and IgL (γ).

9) Biotinylation of MAbs

Purified MAbs were biotinylated to be provided to sandwich ELISA. By using 50 mM of carbonate buffer solution (pH 8.5), it was prepared to 20 mg/ml, 10 μl of NHS-biotin solution dissolved at 3 mg/100 μl in DMSO was added, and the mixture was stirred and then allowed to stand for 2 hours by icing. Subsequently, it was replaced with PBS, to obtain 20 mg/ml.

5-2 Results

1) Characteristics, Classes and Subclasses of Anti N-βLGMAb and anti-R-βLGMAb 13 types of MAbs having specificity against N-βLG were obtained. Specificity against each solid-phased antigen is shown in Table 5.

TABLE 5

| MAbs | N-βLG | R-βLG | D-βLG | Classes, subclasses, and types |
|---|---|---|---|---|
| 751 (PβLG1) | + | + | + | IgG1 (κ) |
| 752 | + | − | − | IgG1 (κ) |
| 753 | + | − | − | IgG1 (κ) |
| 756 | + | − | − | IgG1 (κ) |
| 758 | + | − | − | IgG1 (κ) |
| 759 | + | − | − | IgG1 (κ) |
| 761 | + | + | − | IgG2a (κ) |
| 763 (PβLG2) | + | + | + | IgG1 (κ) |
| 773 | + | + | + | IgG1 (κ) |
| 778 | + | − | − | IgG1 (κ) |
| 781 | + | − | + | IgG1 (κ) |
| 788 | + | + | − | IgG1 (κ) |
| 790 | − | + | − | IgG1 (κ) |
| 796 (PβLG3) | − | + | + | IgG1 (κ) |

2) Combination Conditions in Sandwich ELISA

Each MAb having shown positive reaction to solid-phased antigen was used as solid-phased or biotinylated antibody to select combination of MAbs to detect N-βLG and D-βLG, from the point of view of high sensitivity in sandwich ELISA. As a result, as combinations that can detect N-βLG and D-βLG, plate fixed antibody PLG2 (FERM ABP-10282) and biotinylated antibody PLG1 (FERM ABP-10281) or PLG3 (FERM ABP-1028) were selected. Results of reactivity against N-βLG and D-βLG of PLG2 and PLG 1 by sandwich ELISA are shown in FIG. 3. Further, reactivity against N-βLG and D-βLG of PLG 2 and PLG 3 by sandwich ELISA is shown in FIG. 4.

3) Detection of N-βLG, D-βLG in a MAb Mixed System

Combinations selected by sandwich ELISA (PLG2 for solid-phased, PLG1 and PLG 3 for biotinylated) were used to confirm detection sensitivity of N-βLG and D-βLG. As it is shown in FIGS. 5 and 6, the optical density was higher in a MAb mixed system, for both N-βLG and D-βLG in a MAb mixed system, and it was revealed that it was possible to increase the detection sensitivity.

6. Detection of Whey Protein in Foods by Sandwich ELISA

With the combinations of PLG2 and PLG1, and PLG2 and PLG3 selected in the above 1, it was investigated whether whey protein in actual foods could be detected.

6-1 Materials and Methods

1) Preparation of Meat Product Models

Meat products were selected as food models for quantitative tests, meat product models containing whey protein at each concentration were prepared with a composition shown in Table 6. Fats and muscles were removed from pork loin meat, and minced to 5 mm, and the resultant was used as lean hog. According to each composition, additives were measured, mixed with a food processor, and filled into a vinyl chloride tube, which was heated at 75° C. for 30 min.

TABLE 6

| Raw material | TEST 1 | TEST 2 | TEST 3 | Control |
| --- | --- | --- | --- | --- |
| Lean hog (%) | 83.0 | 83.0 | 83.0 | 83.0 |
| NaCl (%) | 2.0 | 2.0 | 2.0 | 2.0 |
| Sodium polyphosphate (%) | 0.2 | 0.2 | 0.2 | 0.2 |
| Sodium nitrite (ppm) | 120 | 120 | 120 | 120 |
| Sodium ascorbate(ppm) | 300 | 300 | 300 | 300 |
| water | 14.5 | 14.5 | 14.5 | 14.5 |
| Sodium casein (ppm) | 200 | 20 | 2 | 0 |
| Total (%) | 99.762 | 99.744 | 99.7422 | 99.742 |

2) Qualitative Analysis by Sandwich ELISA

Each meat product model was ground until being homogenized with a food processor, and used as a sample for analysis. 1 g of sample was measured and taken, 19 g of PBST (PBS added with 0.5% polyoxyethylene sorbitan monolaurate) containing 10 M of urea, 0.1% of 2-mercaptoethanol was added, and the resultant was stirred for 30 sec with a homogenizer. Then, heat treatment at 100° C. was performed for 1 hour. After cooling, centrifugation was performed at 3,000 rpm for 20 min, and 9.5 ml of PBST was added to 0.5 ml of supernatant and the resultant was used as a sample for ELISA. Serial dilution of whey protein treated with 10 M urea and 0.1% 2-mercaptoethanol was used for standard curve, similarly. Further, comparison was carried out with the case where urea and 2-mercaptoethanol were not used and using sodium casein as a standard curve which was extracted from a sample for analysis by using PBST, and dissolved in PBST.

6-2 Results

The results of using urea and 2-mercaptoethanol for analysis of whey protein in food product model by sandwich ELISA are shown in Table 7, and the results of extracting with only PBST are shown in Table 8.

TABLE 7

|  | TEST 1 | TEST 2 | TEST 3 | Control |
| --- | --- | --- | --- | --- |
| Added amount (ppm) | 200.0 | 20.0 | 2.0 | 0.0 |
| Assay value (ppm) | 170.5 | 18.7 | 2.3 | N.D. *2 |
| Yield (%) *1 | 85.3 | 93.5 | 115.0 | — |

*1: (assay value/added amount) × 100
*2: not detected

TABLE 8

|  | TEST 1 | TEST 2 | TEST 3 | Control |
| --- | --- | --- | --- | --- |
| Added amount (ppm) | 200.0 | 20.0 | 2.0 | 0.0 |
| Assay value (ppm) | 0.1 | N.D. *2 | N.D. | N.D. |
| Yield (%) *1 | 0.05 | — | — | — |

*1: (assay value/added amount) × 100
*2: not detected

From the above results, when urea and 2-mercaptoethanol are added to the extraction solution, whey protein in meat product models can be detected at a high yield, while in PBST extraction, detection was not possible. From these results, it was revealed that it is effective to use urea and 2-mercaptoethanol for extracting whey protein from foods, and as for the characteristics of MAbs used in that case, it is necessary that the MAb are bondable to urea-denatured βLG.

7. Detection of Denatured and Native Sodium Casein by Immunochromatography 7-1 Materials and Methods 1) Preparation of Gold Colloid Labeled and Conjugate Pad MAb solution of PLG1 and PLG3 was prepared to 1 mg/ml with 2 mM of borate buffer solution (pH 9.0). 500 μl of MAb solution was added to 5 ml of gold colloid solution (Sigma) which was previously prepared to pH 9.0 with 0.2 M carbonic potassium solution, and after allowing to react at room temperature for 30 min, 625 μl of 10% BSA solution was added and was further allowed to react for 15 min. It was prepared to OD525=2.0 with 1% BSA solution, and mixed at a ratio of 1:1. The resultant was applied to a glass wool conjugate pad to 68 μl/cm$^2$, and dried.

2) Preparation of Antibody Fixed Membranes

MAb solution of PLG2 was prepared to 4 mg/ml in PBS, and dried by applying linearly on a nitrocellulose membrane. Then, the resultant was blocked for 1 hour, at 37° C., in 10 mM of phosphate buffer (pH 7.5) containing 1% BSA, washed with 10 mM acetate buffer (pH 7.5), then dried.

3) Construction and Estimation of Immunochromato Strips

A sample pad, a conjugate pad, an antibody-fixed membrane and an absorption pad prepared in the above were applied respectively, to make an immunochromato strip. Meat product models prepared in the above 2. were diluted appropriately and used as a test solution.

7-2 Results

With the combination of PLG2 which is a membrane-applied MAb, and PLG1+PLG3 which are gold colloid-labeled MAbs, whey protein could be detected heated as well as non-heated, up to 50 ppb (2 ppm in foods). From this result, it was revealed that immunochromato stip that can respond to any case can be constructed, even when whey protein which has been contaminated during the manufacture process is the target, or when products after heating are the target.

When PBS containing 0.1 M of urea was dropped as a blank in a commercial immunochromato strip to detect allergens, a non-specific band appeared, and it was tested as false positive. Thus, a protein denaturant to detect effectively allergens from food proteins denatured by heating and the like could not be used, and there was a possible risk that subjects detectable as allergens would be limited to a very narrow range e.

EXAMPLE 2

1. Establishment of MAbs Bondable to Denatured/Native Ovalbumin 1-1 Materials and Methods 1) Preparation of Chicken Ovalbumin (Hereinafter Sometimes Referred to as "OA")

Only albumen was collected from fresh chicken eggs, homogenized without beating, saturated sulfate ammonium of an equal amount was added. The resultant was filtrated with a filter paper No. 1 (Advantec Toyo). 0.5 M of sulfate was added to the obtained filtrate, adjusted to pH 4.6 and allow to rest overnight. The precipitates obtained by centrifugation at 8000 rpm×20 min were dissolved in distilled water, and were recrystallized similarly, to obtain crude OA fractions. Crude OAs were further purified by ion exchange chromatography by using TSK gel DEAD 650S (Tosoh). For transfer phase, 50 mM of imidazol-chloride buffer solution (pH 6.4) was used, and OA was fractionated with 0 to 0.3 M linear gradient of NaCl. The resultant was desalted by dialysis, and lyophilized. The lyophilized OAs were used to prepare 0.1% OA solution with saline solution, and aliquoted at 500 µL in 1 ml-volume Eppendorf tubes to make an antigen solution which was stored by freezing at −20° C. until immunization.

2) Immunization

As test animals, 4 BALB/c mice (CLEA Japan) of 6 weeks-old were used. For the primary immunization, an emulsion prepared by adding a complete Freund's adjuvant (Difco) to an Eppendorf tube filled with 500 µl of 0.1% OA at an equal amount, and stirring in a vortex mixer was used. The emulsion was injected intraperitoneally in an amount of 150 µl per mouse. Further, additional immunizations were performed twice at 3 weeks interval. For immunization, an emulsion prepared by adding an incomplete Freund's adjuvant (Difco) to each Eppendorf tube filled with 500 µl of 0.1% OA at an equal amount, and stirring in a vortex mixer was used. The emulsion was injected intraperitoneally in an amount of 150 µl per mouse. Meanwhile, when obtaining anti-denatured OAMAb, a reduced carboxymethylated OA, described in the following, was used only for the last immunization.

3) Measurement of Antibody Titer in Blood

One week after injecting OA as the primary or additional immunization, blood was collected from tail vein of each BALB/c mouse. The blood collected was allowed to stand for 2 hours at room temperature, centrifuged to obtain serum. 10-fold serial dilution of these sera was prepared, and the anti-OA antibody titer in mouse blood was examined by non-competitive ELISA. Meanwhile, alkaline phosphatase labeled-anti mouse IgG (H+L) antibodies (Jackson ImmunoResearch Laboratories Inc.) were used as secondary antibodies.

4) Preparation of Hybridomas

Hybridomas were prepared according to the methods of Keller and Milstein (1975). In other words, 100 µl of 0.1% OA solution was injected to tail-vein of a mouse whose antibody titer has sufficiently increased. Spleen was extracted axenically from the mouse 4 days after intravenous injection. The spleen was chopped, subsequently washed with RPMI 1640, allowed to pass through a sterilized nylon mesh (Cell Strainer, 70 mm, Becton Dickinson), to obtain a spleen cell suspension. Spleen cells were harvested by a centrifugation at 1,000 rpm×10 min, and the cells were counted after resuspending in RPMI1640. The spleen cell suspension and mouse myeloma cells (P3X63Ag8.653) were mixed such that the cell count becomes 10:1, and then centrifuged again at 1,000 rpm×10 min to obtain a pellet. 45% polyethylene glycol with a mean molecular weight of 3,350 was dropped to the pellet to allow a cell fusion. RPMI 1640 was added to the cell solution, which was diluted. A pellet was obtained by centrifugation. A HAT selective consisting of a hybridoma medium (RPMI1640 medium containing 10% bovine fetal serum, 40 mM of 2-mercaptoethanol, 100 U/ml of penicillin, 100 mg/ml of streptomycin) and 100 µM of hypoxanthine, 0.4 µM of aminopterin and 16 µM of thymidine was added to the pellet. The resultant was aliquoted in 24-well cell culture plate (Becton Dickinson) to $5 \times 10^6$ cells/well, and was cultured at 37° C., in the presence of 5% $CO_2$.

5) Cloning by Limiting Dilution

Presence of hybridomas provided as primary antibodies for ELISA and producing anti-OA antibodies was examined in the culture supernatant of each well of cell culture plate. Hybridomas which tested positive against αOA by ELISA were transferred to a 96-well cell culture plate (Becton Dickinson) and cloned by limiting dilution to 0.9 cell/well. Meanwhile, as feeder cells, thymocytes of 4-weeks old BALB/c mouse were added to each well of the 96-well cell culture plate, to $5 \times 10^6$ cells/well. RPMI 1640 media containing 10% of bovine fetal serum, 40 mM of 2-mercaptoethanol, 100 U/ml of penicillin, 100 g/ml of streptomycin were used for culturing cloned hybridomas.

6) Screening of Antibodies

To screen monoclonal antibodies, clones of different specificities were obtained by examining the difference of reactivity of native OA (hereinafter sometimes referred to as "NOA"), or reduced carboxymethylated OA (hereinafter sometimes referred to as "RCMOA"). For RCMOA, 10 mg of purified OA (the above lyophilizates) was measured, 1 ml of 1.4M tris-chloride buffer solution (pH 8.6), 100 µl of 5% EDTA, 1.2 g of urea, 33 µl of 2-mercaptoethanol were added to make a constant volume of 2.5 ml, and a nitrogen gas substitution was performed. Then, the resultant was subjected to a reduction treatment at 37° C. for 1 hour. Further, 89 mg of monoiodoacetic acid dissolved into 300 µl of 1 M NaOH was added to perform a nitrogen gas substitution, and the resultant was carboxymethylated at room temperature for 1 hour, to make a RCMOA. The reactivity against NOA or RCMOA of the culture supernatant was examined by non-competitive ELISA.

7) Collecting Ascitic Fluid and Purification of MAbs

According to Jones et al. (1990), 0.2 ml of incomplete Freund's adjuvant was injected to a BALB/c mouse intraperitoneally. One week after, $5 \times 10^6$ cells/well of cloned hybridomas per mouse were inoculated. After accumulation of ascitic fluid, the fluid was collected with a syringe. The collected ascitic fluid was purified by Protein G column (Amersham pharmacia).

8) Characteristics of MAbs, Classes and Subclasses of MAbs

Solid-phase method and liquid-phase method were used to determine the characteristics of anti-OAMAbs. As a solid-phase method, a method comprising the steps of fixing NOA or RCMOA previously in wells of cell culture plate and to allowing anti-native/denatured OAMAbs to these fixed antigens (NOA or RCMOA), was used. As liquid-phase method, a method comprising the steps of fixing rabbit anti-OA polyclonal antibodies in wells of cell culture plate, and allowing anti-native/denatured OAMAbs to these polyclonal antibodies while NOA or RCMOA are bound. Classes and subclasses of MAbs were determined according to Monoclonal mouse immunoglobulin isotyping kit (Pharmingen) as IgG1, IgG2a, IgG2b, IgG3, IgM, IgA, IgL (κ) and IgL (γ).

9) Biotinylation of MAbs

Purified MAbs were biotinylated to be provided to sandwich ELISA. By using 50 mM of carbonate buffer solution (pH 8.5), it was prepared to 20 mg/ml, 10 µl of NHS-biotin solution dissolved at 3 mg/100 ml in DMSO was added, and the mixture was stirred and then allowed to stand for 2 hours by icing. Subsequently, it was replaced with PBS, to obtain 20 mg/ml.

1-2 Results

1) Characteristics, Classes and Subclasses of Anti-OAMAbs 9 types of MAbs having specificity against NOA and 10 types of MAbs having specificity against RCMOA were obtained. Specificity against each of solid-phased and liquid-phased antigens is shown in Table 9, respectively.

TABLE 9

| MAbs | Solid phased NOA | Liquid phased NOA | Solid phased RCMOA | Liquid phased RCMOA | Classes, sub-classes, and types |
|---|---|---|---|---|---|
| 301B5 | + | + | − | − | IgG1 (κ) |
| 304E4 (PNOA1) | + | + | − | − | IgG1 (κ) |
| 305G5 | + | + | − | − | IgG1 (κ) |
| 306B2 (PNOA2) | + | + | − | − | IgG1 (κ) |
| 307G4 | + | − | − | − | IgG1 (κ) |
| 310G7 | + | + | − | − | IgG1 (κ) |
| 311E11 | + | − | − | − | IgG1 (κ) |
| 314E12 | + | + | − | − | IgG1 (κ) |
| 316G1 | + | + | − | − | IgG1 (κ) |
| 63E5 | + | − | + | + | IgG1 (κ) |
| 65F2 | + | − | + | + | IgG1 (κ) |
| 68G4 | + | − | + | + | IgG1 (κ) |
| 69H6 | + | − | + | + | IgG1 (κ) |
| 74G2 | + | − | + | + | IgG1 (κ) |
| 115F8 | + | − | + | + | IgG1 (κ) |
| 117F9 | + | − | + | + | IgG1 (κ) |
| 119D11 | + | − | + | + | IgG1 (κ) |
| 948G11 (PDOA1) | + | − | + | + | IgG1 (κ) |
| 962B8 (PDOA2) | + | − | + | + | IgG1 (κ) |

2) Combination Conditions

Combinations of MAbs for detecting NOA or MAbs for detecting RCMOA were selected from the point of view of detection sensitivity by sandwich ELISA. As a result, 301B5 and 316G1, or 304E4 (PNOA1; FERM ABP-10265) and 306B2 (PNOA2, FERM ABP-10266) were selected for NOA, and 117F9 and 119D11, or 948G11 (PDOA1; FERM ABP-10275) and 962B8 (PDOA2; FERM ABP-10276) were selected for RCMOA as combinations with high detection sensitivity.

2. Detection of Denatured and Native Antigens by Sandwich ELISA 2-1 Materials and Methods NOA solution was prepared so that purified OA becomes 100 ppb solution with PBS, and 3-fold serial dilution was prepared (serial dilution A). On the other hand, 1 mg of purified OA was measured in a glass tube, 6 g of urea, 0.2 ml of 2-mercaptoethanol, 1 ml of 50 mM tris-hydrochloric buffer solution (pH 8.6) and 1.5 ml of distilled water were added. The resultant was covered with an aluminum cap, and heated at 100° C. for 1 hour in an oil bath, to perform a denaturation treatment. After cooling, the resultant was transferred to 100 ml volume female flask, and messed up to 100 ml with PBS. The resultant was further diluted to 100-fold with PBS and used as urea-denatured OA (hereinafter referred to as "UDOA") 100 ppb solution. Subsequently, 3-fold serial solution was prepared by maintaining the urea concentration to 0.01M (serial dilution B). Further, equivalent amounts of 100 ppb solution of NOA and 100 ppb solution of UODA were mixed (NOA and UDOA become 50 ppb solution, respectively), and 3-fold serial dilution was prepared by maintaining the urea concentration to 0.005 M (serial dilution C).

Conditions of sandwich ELISA are shown in Table 10. Concentration of coating MAb was set to 25 µg/ml when used alone, and 12.5 µg/ml each when mixed, so that the total is 25 µg/mg.

TABLE 10

| Test No. | Coating MAbs | Antigens | Secondary antibodies |
|---|---|---|---|
| Test 1 | 301B5<br>119D11<br>Mixture of 301B5 and 119D11 | Serial dilution A (native) | Mixture of 316G1 and 117F9 |
| Test 2 | 301B5<br>119D11<br>Mixture of 301B5 and 119D11 | Serial dilution B (denatured) | |
| Test 3 | 301B5<br>119D11<br>Mixture of 301B5 and 119D11 | Serial dilution C (native + denatured) | |

2-2 Results

As it is shown in FIG. 7, in Test 1 targeting native OA, curves for 301B5 alone and for a mixture of 301B5 and 119D11, almost lapped over. However, in a thinner condition such as less than 10 ppb, the absorbance level was slightly higher for the curve for 301B5 and 119D11 mixed, compared to the curve for 301B5 alone. Thus, it was considered that the detection sensitivity could be increased. Further, for UDOA in Test 2 targeting denatured OA, no absorbance level was observed for 301B5 alone, and it was thought that 301B5 and 316G1 were not related to UDOA. However, the absorbance level was clearly higher for the curve of a mixture of 301B5 and 119D11 compared to the curve for 119D11 alone. Thus, it was thought that the detection sensitivity could be increased by mixing MAbs (FIG. 8). This result was also observed in Test 3 targeting native/denatured OA, and the absorbance level was clearly higher for a mixture of 301B5 and 119D11, compared to 301B5 alone (FIG. 9). For any of Tests 1 to 3, the concentration of antibody when coated alone was 25 g/ml, and when coated as a mixture of antibodies, the concentration was half, that is 12.5 mg/ml. Therefore, it was revealed that by using a mixed system which increases the types of MAbs, the detection sensitivity of antigen could be enhanced more, even though the antibody concentration is the same or less.

3. Detection of Denatured and Native OA by Immunochromatography 3-1 Materials and Methods 1) Preparation of Gold Colloid Labeled and Conjugate Pad MAb solution of 119D11 and 316G1, alone or mixed, was prepared to 1 mg/ml with 2 mM of borate buffer solution (pH 9.0). 500 µl of MAb solution was added to 5 ml of gold colloid solution (Sigma) which was previously prepared to pH 9.0 with 0.2 M carbonic potassium solution, and after allowing to react at room temperature for 30 min, 625 µl of 10% BSA solution was added and was further allowed to react for 15 min. It was prepared to OD525=1.0 with 1% BSA solution. The resultant was applied to a glass wool conjugate pad (Nihon Millepore) to 68 µl/cm², and dried.

2) Preparation of Antibody Fixed Membranes

MAb solution of 117F9 and 301B5, alone or mixed, was prepared to 4 mg/ml in PBS, and dried by applying linearly on a nitrocellulose membrane. Then, the resultant was blocked for 2 hours at 37° C., in PBS containing 1% BSA and 0.1% Tween 20, washed with PBS and dried.

3) Construction and Estimation of Immunochromato Strips

Beside a conjugate pad and an antibody-fixed membrane prepared in the above, a sample pad made by glass wool for test solution spot, an absorption pad made by glass wool for absorption of test solution were prepared. The sample pad, conjugate pad, antibody-fixed membrane and absorption pad were applied subsequently to make an immunochromato strip. NOA and UDOA prepared in the above 2 were diluted appropriately and used as a test solution.

3-2 Results

With the combination of 301B5 and gold colloid labeled 316G1, NOA could be detected up to 10 ppb. However, UDOA was not detected, even in an amount of 1 ppm. On the other hand, with the combination of 117F9 and gold colloid labeled 119D11, UDOA could be detected up to 10 ppb, while NOA was not detected even in an amount of 1 ppm. On the contrary, when an immunochromato strip was prepared by using a fixed antibody mixture of 301B5 and 117F9, and a gold colloid antibody mixture of 316G1 and 119D11, denatured OA or native OA could be detected up to 10 ppb. By combining MAbs bondable to denatured OA with MAbs bondable to native OA, it is possible to construct an immunochromato strip that can respond to any case, even if a denatured albumen mixed during manufacture is the target, or if a product after heating is the target.

When PBS containing only 0.01 M of urea as a blank was dropped to a commercial immunochromato strip for detecting allergens, a non-specific band appeared, and it was tested as false positive. Thus, urea which is a protein denaturant to extract albumen allergens which has been in solubilized by heat, etc. could not be used, and there was a possible risk that subjects detectable as allergens would be limited to a very narrow range.

4. Establishment of MAb Bondable to Denatured/Native Ovomucoid 4-1 Materials and Methods 1) Preparation of Chicken Ovomucoid (Hereinafter Referred to as "OM")

Only albumen was collected from fresh chicken egg, homogenized without beating, and the resultant was mixed with an equivalent amount of 0.1 M acetate buffer solution (pH 3.8). Subsequently, dialysis was performed to 0.1 M acetate buffer, and the resultant was centrifuged at 8,000 rpm×20 min to collect the supernatant. Further, the resultant was purified by ion exchange chromatography by using TSK gel DEAE 650S (Tosoh). For transfer phase, 50 mM of imidazol-chloride buffer solution (pH 6.4) was used, and OM was fractionated with 0 to 0.3 linear gradient of NaCl. The resultant was desalted by dialysis and lyophilized, which were used as native OM (hereinafter sometimes referred to as "NOM"). 1 mg of the purified OM was measured, to which 6 g of urea, 0.2 ml of mercapto-ethanol, 1 ml of 50 mM trischloride buffer and 1.5 ml of distilled water were added. The resultant was covered with an aluminum cap, heated in an oil bath at 100° C. for 1 hour to perform a denaturation treatment, to make a urea-denatured OM (hereinafter sometimes referred to as "DOM"). 0.1% solution of these lyophilizates was prepared with a saline solution, aliquoted at 500 µl in 1 ml-volume Eppendorf tubes to make an antigen solution which was stored by freezing at −20° C. until immunization.

2) Immunization

As test animals, 4 BALB/c mice (CLEA Japan) of 6 weeks-old were used. For the primary immunization, an emulsion prepared by adding a complete Freund's adjuvant (Difco) to an Eppendorf tube filled with 500 µl of 0.1% NOM or DOM, and stirring in a vortex mixer was used. The emulsion was injected intraperitoneally in an amount of 150 µl per mouse.

Further, additional immunizations were performed twice at 3 weeks interval. For immunization, an emulsion prepared by adding an incomplete Freund's adjuvant (Difco) to each Eppendorf tube filled with 500 µl of 0.1% NOM or DOM at an equal amount, and stirring in a vortex mixer was used. The emulsion was injected intraperitoneally in an amount of 150 µl per mouse.

3) Measurement of Antibody Titer in Blood

One week after injecting NOM or DOM as the primary or additional immunization, blood was collected from tail vein of each BALB/c mouse. The blood collected was allowed to stand for 2 hours at room temperature, centrifuged to obtain serum. 10-fold serial dilution of these sera was prepared, and the anti-OM antibody titer in mouse blood was examined by non-competitive ELISA. Meanwhile, alkaline phosphatase labeled-anti mouse IgG (H+L) antibodies (Jackson ImmunoResearch Laboratories Inc.) were used as secondary antibodies.

4) Preparation of Hybridomas

Hybridomas were prepared according to the methods of Keller and Milstein (1975). In other words, 100 ml of 0.1% NOM solution or DOM solution was injected to tail-vein to a mouse which antibody titer has sufficiently increased. Spleen was extracted axenically from the mouse 4 days after intravenous injection. The spleen was chopped, subsequently washed with RPMI 1640, allowed to pass through a sterilized nylon mesh (Cell Strainer, 70 mm, Becton Dickinson), to obtain a spleen cell suspension. Spleen cells were harvested by a centrifugation at 1,000 rpm×10 min, and the cells were counted after resuspending in RPMI 1640. The spleen cell suspension and mouse myeloma cells (P3X63Ag8.653) were mixed such that the cell count becomes 10:1, and then centrifuged again at 1,000 rpm×10 min to obtain a pellet. 45% polyethylene glycol with a mean molecular weight of 3,350 was dropped to the pellet to allow a cell fusion. RPMI 1640 was added to the cell solution, which was diluted. A pellet was obtained by centrifugation. A HAT selective medium consisting of a hybridoma medium (RPMI1640 medium containing 10% bovine fetal serum, 40 mM of 2-mercaptoethanol, 100 U/ml of penicillin, 100 mg/ml of streptomycin) and 100 µM of hypoxanthine, 0.4 µM of aminopterin and 16 µM of thymidine was added to the pellet. The resultant was aliquoted in 24-well cell culture plate (Becton Dickinson) to $5\times10^6$ cells/well, and was cultured at 37° C., in the presence of 5% $CO_2$.

5) Cloning by Limiting Dilution

Presence of hybridomas provided as primary antibodies of ELISA and producing anti-NOM antibodies or anti-DOM antibodies was examined in the culture supernatant of each well of cell culture plate. Hybridomas which tested positive against NOM or DOM by ELISA were transferred to a 96-well cell culture plate (Becton Dickinson) and cloned by limiting dilution to 0.9 cell/well. Meanwhile, as feeder cells, thymocytes of 4-weeks old BALB/c mouse were added to each well of the 96-well cell culture plate, to $5\times10^6$ cells/well. RPMI 1640 media containing 10% of bovine fetal serum, 40 mM of 2-mercaptoethanol, 100U/ml of penicillin, 100 g/ml of streptomycin were used for culturing the cloned hybridomas.

6) Collecting Ascitic Fluid and Purification of MAb

According to Jones et al. (1990), 0.2 ml of incomplete Freund's adjuvant was injected to a BALB/c mouse intraperitoneally. One week after, $5\times10^6$ cells/well of cloned hybridomas were inoculated per mouse. After accumulation of ascitic fluid, the fluid was collected with a syringe. The collected ascitic fluid was purified by Protein G column (Amersham pharmacia).

8) Characteristics of MAbs, Classes and Subclasses of MAbs

Solid-phase method and liquid-phase method were used to determine the characteristics of anti-NOMMAbs and anti-DOMMAbs. As solid-phase method, a method comprising the steps of fixing NOM or DOM previously in wells of cell culture plate and allowing MAbs to react to these fixed NOM or DOM, was used. As liquid-phase method, a method comprising the steps of fixing rabbit anti-ovomucoid polyclonal antibodies in wells of cell culture plate, and allowing MAbs react to these polyclonal antibodies while NOM or DOM are bound. Classes and subclasses of MAbs were determined according to Monoclonal mouse immunoglobulin isotyping kit (Pharmingen) as IgG1, IgG2a, IgG2b, IgG3, IgM, IgA, IgL (κ) and IgL (γ).

8) Biotinylation of MAbs

Purified MAbs were biotinylated to be provided to sandwich ELISA. By using 50 mM of carbonate buffer solution (pH 8.5), it was prepared to 20 mg/ml, 10 ml of NHS-biotin solution dissolved at 3 mg/100 μl in DMSO was added, and the mixture was stirred and then allowed to stand for 2 hours by icing. Subsequently, it was replaced with PBS, to obtain 20 mg/ml.

4-2 Results

1) Characteristics, Classes and Subclasses of Anti-NOM-MAbs and Anti-DOMMabs 7 types of MAbs having specificity against NOM and 10 types of MAbs having specificity against DOM were obtained. Specificity against each of solid-phased and liquid-phased antigens is shown in Table 11, respectively.

TABLE 11

| MAbs | Native solid phased OM | Native liquid phased OM | Denatured solid phased OM | Denatured liquid phased OM | Classes, subclasses, and types |
|---|---|---|---|---|---|
| 47E5 (PNOM1) | + | + | − | − | IgG2a (κ) |
| 50A12 (PNOM2) | + | + | − | − | IgG1 (κ) |
| 52C6 | + | + | − | − | IgG1 (κ) |
| 53E11 | + | − | − | − | IgG1 (κ) |
| 56E4 | + | + | − | − | IgM (κ) |
| 57G12 | + | − | − | − | IgM (κ) |
| 60C11 | + | − | − | − | IgG1 (κ) |
| 628E1 (PDOM1) | − | − | + | + | IgG1 (κ) |
| 640G11 | − | − | + | + | IgG1 (κ) |
| 645B5 | − | − | + | + | IgG1 (κ) |
| 648A9 (PDOM2) | − | − | + | + | IgG1 (κ) |
| 658B6 | − | − | + | + | IgG1 (κ) |
| 663A9 | − | − | + | + | IgG1 (κ) |
| 668D6 | − | − | + | + | IgG1 (κ) |
| 670E1 | − | − | + | + | IgG1 (κ) |
| 671H8 | − | − | + | + | IgG1 (κ) |
| 674A4 | − | − | + | + | IgG1 (κ) |

2) Combination Conditions

Combinations of MAbs for detecting NOM were selected from the point of view of detection sensitivity by sandwich ELISA. As a result, the combination of 47E5 (PNOM1; FERM ABP-10279) and 50A12 (PNOM2; FERM ABP-10280) was selected as a combination with high detection sensitivity. Further, sandwich ELISA was performed by using the above 10 monoclonal antibodies, and those having the highest sensitivity, 628E1 (PDOM1; FERM ABP-10277) and 648A9 (PDOM2; FERM ABP-10278) were selected as a combination having high detection sensitivity.

3) Reactivity of each Monoclonal Antibody and OM by Sandwich ELISA

By sandwich ELISA of PNOM1 and PNOM2, native ovomucoid was detected, while denatured ovomucoid was not detected at all (FIG. 10). Further, by sandwich ELISA of PDOM1 and PNOM2, denatured OM was detected, but for native OM, sensitivity was low, in an amount between 10 to 100 ppb (FIG. 11). However, by sandwich ELISA wherein each monoclonal antibody is combined, by using PNOM2 and PDOM2 as plate antibodies, and PNOM1 and PDOM1 as biotin antibodies, detection sensitivity for native OM at 10 to 100 ppb was especially enhanced (FIG. 12).

5. Detection of Albumen Using OM as Index by Immunochromatography 5-1 Materials and Methods 1) Preparation of Gold Colloid Labels and Conjugate Packs MAb solution of PNOM1 was prepared to 1 mg/ml with 2 mM of borate buffer solution (pH 9.0). 500 μl of MAb solution was added to 5 ml of gold colloid solution (Sigma) which was previously prepared to pH 9.0 with 0.2 M carbonic potassium solution, and after allowing to react at room temperature for 30 min, 625 μl of 10% BSA solution was added and was further allowed to react for 15 min. Centrifugation was performed to OD525=1.0 with 1% BSA solution. The resultant was applied to a glass wool conjugate pad to 68 μl/cm², and dried.

2) Preparation of Antibody Fixed Membranes

MAb solution of PNOM2 was prepared to 4 mg/ml in PBS, and dried by applying linearly on a nitrocellulose membrane. Then, the resultant was blocked for 2 hours, at 37° C., in PBS containing 1% BSA and 0.1% Tween 20.

3) Construction and Estimation of Immunochromato Strips

Besides a conjugate pad and an antibody-fixed membrane prepared in the above, a sample pad made by glass wool for test solution spot, an absorption pad made by glass wool for absorption of test solution were prepared. The sample pad, conjugate pad, antibody-fixed membrane and absorption pad were applied subsequently to make an immunochromato strip. 0.1% solution of lyophilized albumen powder, treated for 1 hour at room temperature, 50° C., 75° C. and 100° C., respectively, was diluted appropriately and used as a test solution.

5-2 Results

With the combination of PNOM1 and gold colloid labeled PNOM2, albumen solution which has been treated for 1 hour at room temperature and 50° C. could be detected up to 10 ppb. Further, albumen which has been treated for 1 hour at 75° C. and 100° C., could be detected up to 100 ppb. From this result, for foods which have been subjected to heat-treatment corresponding to a treatment for 1 hour at 100° C., even by not using a denaturant such as urea, albumen could be detected up to 100 ppb by a simple extraction by using an immunochromato strip of this anti-OMMAb. However, as detection was not possible with a heat treatment exceeding 100° C. by an immunochromatography of OM, a solubilized treatment by urea, such as in the above, was necessary.

6. Effect of Using in Combination Anti-OA MAbs and Anti-OM Mabs 6-1 Methods

From the above result, an immunochromato strip using PNOA1, and a fixed antibody mixture of PDOA1 and PNOM1, as well as PNOA2 and a gold colloid antibody mixture of PDOA2 and PNOM2 were prepared as mentioned in the above, and detection of albumen was tried.

6-2 Results

As it is shown in the above, with the combinations PNOA1 and PNOA2, PDOA1 and PDOA2, and PNOM1 and PNOM2, the desired denatured/native OA or OM could be detected with respective sensitivity. From this result, a method for detecting albumen was developed, wherein MAbs against native OA and OM react when it is non-heated, and MAbs against native/denatured OA and OM reacts when it is 50° C. to 100° C., and denatured OA reacts by a solubilization treatment by urea when the temperature is higher than that, during the manufacturing process of processed foods.

EXAMPLE 3

1. Establishment of MAbs Bondable to Denatured/Native Flour Gliadin 1-1 Materials and Methods 1) Preparation of Flour Gliadin (Hereinafter Referred to as "GL")

2-fold amount of n-butanol was added to flour for defatting, and the resultant was allowed to air dry for overnight. 2-fold amount of 0.1% sodium chloride solution was added to the obtained defatted flour and the resultant was centrifuged at 10,000 rpm×15 min. 20-fold amount of 0.01 N acetate was added to the obtained precipitates, and the mixture was stirred and centrifuged at 10,000 rpm for 15 min. The obtained supernatant was dialyzed with distilled water and lyophilized. Ethanol was added to the obtained lyophilizates to 70%, and the resultant was centrifuged at 10,000 rpm×15 min. The obtained supernatant was dialyzed with distilled water to obtain crude GL fractions. The GL fractions were further purified by gel filtration using Sephacryl S-200HR (Amersham Biosciences). For transfer phase, Gls were fractionated with 0.1 N acetate, dialyzed with distilled water and lyophilized. 0.1% solution of the lyophilizates was prepared with saline, and aliquoted at 500 µl to 1 ml-volume Eppendorf tubes. The resultant was stored by freezing at −20° C. until immunization and was used as antigen solution.

2) Immunization

As test animals, 5 BALB/c mice (CLEA Japan) of 5 weeks-old were used. For the primary immunization, an emulsion prepared by adding a complete Freund's adjuvant (Difco) to an Eppendorf tube filled with 500 µl of 0.1% GL at an equal amount, and stirring in a vortex mixer was used. The emulsion was injected intraperitoneally in an amount of 150 µl per mouse. Further, additional immunizations were performed twice at 3 weeks interval. For immunization, an emulsion prepared by adding an incomplete Freund's adjuvant (Difco) to an Eppendorf tube filled with 500 µl of 0.1% GL at an equal amount, and stirring in a vortex mixer was used. The emulsion was injected intraperitoneally in an amount of 150 µl per mouse.

3) Measurement of Antibody Titer in Blood

One week after injecting GL as the primary or additional immunization, blood was collected from tail vein of each BALB/c mouse. The blood collected was allowed to stand for 2 hours at room temperature, centrifuged to obtain serum. 10-fold serial dilution of these sera was prepared, and the anti-GL antibody titer in mouse blood was examined by non-competitive ELISA. Meanwhile, alkaline phosphatase labeled-anti mouse IgG (H+L) antibodies (Jackson ImmunoResearch Laboratories Inc.) were used as secondary antibodies.

4) Preparation of Hybridomas

Hybridomas were prepared according to the method of Keller and Milstein (1975). In other words, 100 µl of 0.1% GL solution was injected to tail-vein to a mouse whose antibody titer has sufficiently increased. Spleen was extracted axenically from the mouse 4 days after intravenous injection. The spleen was chopped, subsequently washed with RPMI 1640, allowed to pass through a sterilized nylon mesh (Cell Strainer, 70 mm, Becton Dickinson), to obtain a spleen cell suspension. Spleen cells were harvested by a centrifugation at 1,000 rpm×10 min, and the cells were counted after resuspending in RPMI 1640. The spleen cell suspension and mouse myeloma cells (P3X63Ag8.653) were mixed such that the cell count becomes 10:1, and then centrifuged again at 1,000 rpm×10 min to obtain a pellet. 45% polyethylene glycol with a mean molecular weight of 3,350 was dropped to the pellet to allow a cell fusion. RPMI 1640 was added to the cell solution, which was diluted. A pellet was obtained by centrifugation. A HAT selective medium consisting of a hybridoma medium (RPMI1640 medium containing 10% bovine fetal serum, 40 mM of 2-mercaptoethanol, 100 U/ml of penicillin, 100 mg/ml of streptomycin) and 100 µM of hypoxanthine, 0.4 µM of aminopterin and 16 µM of thymidine was added to the pellet. The resultant was aliquoted in 24-well cell culture plate (Becton Dickinson) to $5 \times 10^6$ cells/well, and was cultured at 37° C., in the presence of 5% $CO_2$.

5) Cloning by Limiting Dilution

Presence of hybridomas provided as primary antibodies of ELISA and producing anti-GL antibodies was examined in the culture supernatant of each well of cell culture plate. Hybridomas which tested positive against GL by ELISA were transferred to a 96-well cell culture plate (Becton Dickinson) and cloned by limiting dilution to 0.9 cell/well. Meanwhile, as feeder cells, thymocytes of 4-weeks old BALB/c mouse were added to each well of the 96-well cell culture plate, to $5 \times 10^6$ cells/well. RPMI 1640 medium containing 10% of bovine fetal serum, 40 mM of 2-mercaptoethanol, 100 U/ml of penicillin and 100 µg/ml of streptomycin was used for culturing the cloned hybridomas.

6) Screening of Antibodies

To screen monoclonal antibodies, clones of different specificities were obtained by examining the difference of reactivity against native GL (hereinafter referred to as "NGL"), reduced carboxymethylated GL (hereinafter referred to as "RCMGL"), GL solubilized with 0.1 M acetate (hereinafter referred to as "AGL"), GL solubilized with 70% ethanol (hereinafter referred to as "EGL"), and GL solubilized with a denaturant (hereinafter referred to as "DGL"). For RCMGL, 10 mg of purified GL was measured, 1 ml of 1.4 M tris-hydrochloric acid (pH8.6), 100 µl of 5% EDTA, 1.2 f of urea and 33 µl of 2-mercaptoethanol were added to make a constant volume of 2.5 ml, and nitrogen gas substitution was performed. The resultant was subjected to a reduction treatment at 37° C. for 1 hour. Further, 89 mg of monoiodoacetic acid dissolved into 300 µl of 1M NaOH was added to perfume a nitrogen gas substitution and the resultant was carboxymethylated at room temperature for 1 hour, to obtain RCMGL. Reactivity against NGL, RCMGL, AGL, EGL and DGL of the culture supernatant was examined by non-competitive ELISA.

7) Collecting Ascitic Fluid and Purification of MAbs

According to Jones et al. (1990), 0.2 ml of incomplete Freund's adjuvant was injected to BALB/c mouse intraperitoneally. One week after, $5 \times 10^6$ cells/well of cloned hybridomas per mouse were inoculated. After accumulation of ascitic fluid, fluid was collected with a syringe. The collected ascitic fluid was purified by Protein G column (Amersham pharmacia).

8) Classes, Subclasses and Types of MAbs

Classes and subclasses of MAbs were determined according to Monoclonal mouse immunoglobulin isotyping kit (Pharmingen) as IgG1, IgG2a, IgG2b, IgG3, IgM, IgA, IgL (κ) and IgL (γ).

9) Biotinylation of MAbs

Purified MAbs were biotinylated to be provided to sandwich ELISA. By using 50 mM of carbonate buffer solution (pH 8.5), it was prepared to 20 mg/ml, 10 µl of NHS-biotin solution dissolved at 3 mg/100 ml in DMSO was added, and the mixture was stirred and then allowed to stand for 2 hours by icing. Subsequently, it was replaced with PBS, to 20 mg/ml.

2-2 Results

1) Selection of MAbs

Gliadin (GL) which is a main allergen of flour is a protein insoluble to water, and soluble to acetate or ethanol. Therefore, GL solubilized in PBS (NGL), reduced carboxymethylated GL (RCMGL), GL solubilized with 0.1M acetate (AGL), GL solubilized with 70% ethanol (EGL), GL solubilized with a denaturant (DGL) were prepared and it was investigated to which state of GL the antibody binds specifically. The results of direct ELISA for anti-GLMAbs against GL in each of the above states are shown in Table 12. As it is shown in Table 1, PGL1 (FERM ABP-10267), PGL2 (FERM ABP-10268), PGL4 and PGL7 which are MAbs that bind to GL in any of the states, were selected.

TABLE 12

|      | NGL | RGL | AGL | EGL | DGL | Classes, subclasses and types |
|------|-----|-----|-----|-----|-----|-------------------------------|
| PGL1 | ○   | ○   | ○   | ○   | ○   | IgG1 (κ)                      |
| PGL2 | ○   | ○   | ○   | ○   | ○   | IgG1 (κ)                      |
| PGL3 | ○   | Δ   | ○   | X   | ○   | IgG1 (κ)                      |
| PGL4 | ○   | ○   | ○   | ○   | ○   | IgG1 (κ)                      |
| PGL5 | ○   | Δ   | ○   | Δ   | Δ   | IgG1 (κ)                      |
| PGL6 | ○   | X   | ○   | ○   | ○   | IgG1 (κ)                      |
| PGL7 | ○   | ○   | ○   | ○   | ○   | IgG1 (κ)                      |
| PGL8 | ○   | Δ   | ○   | X   | ○   | IgG1 (κ)                      |

2) Combination Conditions in Sandwich ELISA

By using PGL1, PGL2, PGL4 and PGL7 selected by direct ELISA, sandwich ELISA was performed to all of the MAb combinations. NGL, RCMGL, AGL, EGL and DGL were used for gliadin. As a result, the combination with which GL could be detected highly in any state was the combination of PGL1 and PGL2. The results of sandwich ELISA using PGL1 and PGL2 are shown in Table 13. For other combinations, all of GLs could not be detected or the detection sensitivity was very low by sandwich ELISA. From the above result, PGL1 and PGL2 were selected as MAbs detecting GL contained in various states in foods.

2. Difference of Epitopes Recognized by PGL1 and PGL2

In order to determine epitopes recognized by each antibody, by immunoblotting, immnoblotting was performed following A-PAGE and electro blotting. First, flour gliadin was separated by A-PAGE according to Lafiandra, D. & Kasarda, D. D. (Cereal Chemistry, 62, 314-319, 1985). By using the separated gel, it was transcribed on a PVDF membrane by electro blotting. After allowing to react the culture supernatant of PGL1 and PGL2 to the transcribed PVDF membrane, the recognized epitopes were confirmed by coloring. As a result, as it is shown in FIG. 14, the protein degradation band recognized by PGL1 was not recognized by PGL2. From this result, it was revealed that PGL1 and PGL2 recognize different epitopes.

3. Detection of Denatured and Native GL by Immunochromatography 3-1 Materials and Methods 1) Preparation of Gold Colloid Labels and Conjugate Pads PLG1 (or PLG2) solution was prepared to 1 mg/ml with 2 mM of borate buffer solution (pH 9.0). 500 µl of MAb solution was added to 5 ml of gold colloid solution (Sigma) which was previously prepared to pH 9.0 with 0.2 M carbonic potassium solution, and after allowing to react at room temperature for 30 min, 625 µl of 10% BSA solution was added and was further allowed to react for 15 min. Centrifugation was performed and it was prepared to OD525=1.0 with 1% BSA solution. The resultant was applied to a glass wool conjugate pad (Japan Millipore) to 68 µl/cm$^2$, and dried.

2) Preparation of Antibody Fixed Membranes

PGL2 (or PGL1) solution was prepared to 4 mg/ml in PBS, applied linearly on a nitrocellulose membrane and dried. Then, the resultant was blocked for 2 hours, at 37° C., in PBS containing 1% BSA and 0.1% Tween 20, and washed with PBS and dried.

3) Construction and Estimation of Immunochromato Strips

Beside a conjugate pad and an antibody fixed membrane prepared in the above, a sample pad made by glass wool for test solution spot, an absorption pad made by glass wool for absorption of test solution were prepared. The sample pad, conjugate pad, antibody-fixed membrane and absorption pad were applied in this order to make an immunochromato strip.

The test solution was prepared as follows: 20-fold amount of PBST (0.5% polyoxyethylene sorbitan monolaurate added to PBS) was added to flour, the mixture was stirred at 4° C. overnight, and the supernatant which had been defatted after centrifugation was collected. The resultant was dialyzed and the lyophilizates were prepared as a flour extract. By using the prepared flour extract, the solution which has been diluted with PBS was used as a native flour extract, and the solution which had been solubilized with a denaturant as denatured flour extract.

3-2 Results

As GL of various states were detected by sandwich ELISA, a detection system by immunochromatography was established as an easier detection method, and estimated. For estimation, commercial A and B, which use the same antibodies as allergen detection kits currently on market were compared. The results are shown in Table 13. In Table 13, "non-specific reaction" is marked "present" when it was tested positive with only buffer solution. As a result, with commercial A, native flour extract was detected, while denatured flour extract could not be determined as no non-specific reaction was observed. Further, with commercial B, native flour extract was not detected even in an amount of 1 ppm, and a denatured flour extract could not determined as no non-specific reaction was observed. With a method using a kit of the present invention, both native flour extract and denatured flour extract could be detected up to 50 bbp. Further, non-specific reaction was not observed for denatured flour extract.

TABLE 13

|                                | 1 ppm | 100 ppb | 50 ppb | 10 ppb | Non-specific reaction |
|--------------------------------|-------|---------|--------|--------|----------------------|
| Flour extract (native)         |       |         |        |        |                      |
| Method of the present invention| ○     | ○       | ○      | X      | none                 |
| Commercial A                   | ○     | ○       | ○      | X      | none                 |
| Commercial B                   | X     | X       | X      | X      | none                 |
| Flour extract (denatured)      |       |         |        |        |                      |
| Method of the present invention| ○     | ○       | ○      | Δ      | none                 |
| Commercial A                   | —     | —       | —      | —      | present              |
| Commercial B                   | —     | —       | —      | —      | present              |

Next, supposing to detect allergens from actual foods, estimation was performed by using commercially available bread. For estimation, commercial A and B, which use allergen detection kits currently on market were compared. The results are shown in Table 14. In Table 14, "non-specific reaction" is indicated "present" when it was tested positive with only a buffer solution. As the protein in bread is about 8%, the concentrations in the following are a number based on the estimation that the content of 8% was fully extracted. As a result of estimation, with commercial A, native bread could not be detected at a concentration less than 4 ppm. For denatured bread, non-specific reaction was observed and determination was not possible. With commercial B, detection at about 4 ppm was possible while the detection was not possible at other concentrations. For denatured bread, non-specific reaction was observed and determination was not possible. With the method using a kit of the present invention, both native bread and denatured bread could be detected even at a concentration is as low as 40 ppb. Further, non-specific reaction was not observed for denatured bread, and detection was possible.

TABLE 14

|  | 400 ppm | 4 ppm | 400 ppb | 40 ppb | Non-specific reaction |
| --- | --- | --- | --- | --- | --- |
| Native bread (concentration is converted to protein concentration) | | | | | |
| Method of the present invention | ◯ | ◯ | ◯ | Δ | none |
| Commercial A | X | ◯ | X | X | none |
| Commercial B | ◯ | X | X | X | none |
| Denatured bread (concentration is converted to protein concentration) | | | | | |
| Method of the present invention | ◯ | ◯ | ◯ | Δ | none |
| Commercial A | — | — | — | — | present |
| Commercial B | — | — | — | — | present |

EXAMPLE 4

1. Establishment of Anti-24 kDa Protein MAb and Anti-76 kDa Protein MAb
1-1 Materials and Methods
1) Preparation of Buckwheat 24 kDa Protein MAbs and Anti76 kDa Protein MAb 5-fold amount of purified water was added to commercially available buckwheat flour. The mixture was stirred and then centrifuged at 12000 rpm to obtain precipitates. 5-fold amount of 1M sodium chloride was added to the obtained precipitates. The mixture was stirred and then centrifuged at 12000 rpm to obtain supernatants. The supernatants were desalted by dialysis, lyophilized, and the obtained fractions were used as buckwheat crude protein fractions. The buckwheat crude protein fractions were further purified by using Prep Cell 960 (BioRad). Purification of 24 kDa protein was performed as follows: buckwheat crude protein fractions were dissolved into a sample buffer containing 2.0% SDS and 5% 2-mercaptoethanol, and the resultant was heated at 95° C. for 4 min, and used as a sample. The sample was fractionated with Prep Cell 960 by using acrylamide 12% separation gel, to obtain 24 kDa protein. Purification of 76 kDa Protein was performed as follows: buckwheat crude fractions were dissolved into a sample buffer containing 2.0% SDS and not containing 2-mercapto ethanol, and the resultant was used as a sample. The sample was fractionated with Prep Cell 960 using acrylamide 12% separation gel, to obtain 76 kDa protein. Each of the obtained fractions was lyophilized after dialysis. 0.1% 24 kDa protein solution and 0.1% 76 kDa protein solution were prepared by using these lyophilizates with saline, and were aliquoted at 500 μl into 1 ml-volume Eppendorf tubes to make an antigen solution. The solution was stored by freezing at −20° C. until immunization.

2) Immunization

As test animals, 5 BALB/c mice (CLEA Japan) of 5 weeks-old were used. For the primary immunization, an emulsion prepared by adding a complete Freund's adjuvant (Difco) to an Eppendorf tube each filled with 500 μl of 0.1% 24 kDa protein solution and 0.1% 76 kDa protein solution at an equal amount, and stirring in a vortex mixer was used. The emulsion was injected intraperitoneally in an amount of 150 μl per mouse. Further, additional immunizations were performed twice at 3 weeks interval. For immunization, an emulsion prepared by adding an incomplete Freund's adjuvant (Difco) to each Eppendorf tube filled with 500 μl of 0.1% 24 kDa protein solution and 0.1% 76 kDa protein solution at an equal amount, and stirring in a vortex mixer was used. The emulsion was injected intraperitoneally in an amount of 150 μl per mouse.

3) Measurement of Antibody Titer in Blood

One week after injecting 24 kDa protein solution or 76 kDa protein solution as the primary or additional immunization, blood was collected from tail vein of each BALB/c mouse. 10-fold serial dilution of these sera was prepared, and the anti-24 kDa protein antibody titer and anti-76 kDa protein antibody titer in mouse blood was examined by non-competitive ELISA. Meanwhile, alkaline phosphatase labeled-anti mouse IgG (H+L) antibodies (Jackson ImmunoResearch Laboratories Inc.) were used as secondary antibodies.

4) Preparation of Hybridomas

Hybridomas were prepared according to the method of Keller and Milstein (1975). In other words, 100 μl of 0.1% 24 kDa protein solution and 0.1% 76 kDa protein solution were injected to tail-vein to a mouse which antibody titer has sufficiently increased. Spleen was extracted axenically from the mouse 4 days after intravenous injection. The spleen was chopped, subsequently washed with RPMI 1640, allowed to pass through a sterilized nylon mesh (Cell Strainer, 70 mm, Becton Dickinson), to obtain a spleen cell suspension. Spleen cells were harvested by a centrifugation at 1,000 rpm×10 min, and the cells were counted after resuspending in RPMI 1640. The spleen cell suspension and mouse myeloma cells (P3X63Ag8.653) were mixed such that the cell count becomes 10:1, and then centrifuged again at 1,000 rpm×10 min to obtain a pellet. 45% polyethylene glycol with a mean molecular weight of 3,350 was dropped to the pellet to allow a cell fusion. RPMI 1640 was added to the cell solution, which was diluted. A pellet was obtained by centrifugation. A HAT selective medium consisting of a hybridoma medium (RPMI1640 medium containing 10% bovine fetal serum, 40 mM of 2-mercaptoethanol, 100 U/ml of penicillin, 100 mg/ml of streptomycin), 100 μM of hypoxanthine, 0.4 μM of aminopterin and 16 μM of thymidine was added to the pellet. The resultant was aliquoted in 24-well cell culture plate (Becton Dickinson) to 5×10⁶ cells/well, and was cultured at 37° C., in the presence of 5% $CO_2$.

5) Cloning by Limiting Dilution

Presence of hybridomas provided as primary antibodies of ELISA and producing anti-24 kDa protein antibodies or anti-76 kDa protein antibodies was examined in the culture supernatant of each well of cell culture plate. Hybridomas which tested positive against 24 kDa protein or 76 kDa protein by ELISA were transferred to a 96-well cell culture plate (Becton Dickinson) and cloned by limiting dilution to 0.9 cell/well. Meanwhile, as feeder cells, thymocytes of 4-weeks old BALB/c mouse were added to each well of the 96-well cell culture plate, to 5×10⁶ cells/well. RPMI 1640 medium containing 10% of bovine fetal serum, 40 mM of 2-mercaptoethanol, 100 U/ml of penicillin, 100 g/ml of streptomycin was used for culturing cloned hybridomas.

6) Screening of Antibodies

To screen monoclonal antibodies, clones of different specificities were obtained by examining the difference of reactivity against 24 kDa protein, 76 kDa protein, buckwheat crude protein diluted in PBS (hereinafter sometimes referred to as "NBW"), or buckwheat crude protein solubilized with a denaturant (hereinafter sometimes referred to as "DBW"). Buckwheat crude proteins were prepared by adding 20-fold amount of PBST to buckwheat flour, stirring the mixture overnight at 4° C., recovering the supernatant which has been defatted after centrifugation. The resultant was dialyzed and lyophilized, and was prepared as buckwheat flour extract. Solubilization with a denaturant was performed as follows: 10 mg of buckwheat crude protein was measured, 6 g of urea, 0.2 ml of 2-mercapto ethanol, 1 ml of 50 m Tris-HCl buffer solution (pH 8.6) and 1.5 ml of distilled water were added. The resultant was covered with an aluminum cap, and heated at 100° C. for 1 hour in an oil bath to perform a denaturation treatment. The resultant was used as DBW. Reactivity against 24 kDa protein, 76 kDa protein, NBW and DBW in the supernatant was investigated by non-competitive ELISA.

7) Collecting Ascitic Fluid and Purification of MAb

According to Jones et al. (1990), 0.2 ml of incomplete Freund's adjuvant was injected to a BALB/c mouse intraperitoneally. One week after, $5 \times 10^6$ cells/well of cloned hybridomas per mouse were inoculated. After accumulation of ascitic fluid, fluid was collected with a syringe. The collected ascitic fluid was purified by Protein G column (Amersham pharmacia).

8) Characteristics of MAbs; Classes, Subclasses and Types of MAbs

Solid phase method was used to determine the characteristics of anti-24 kDa protein MAb or anti-76 kDa protein MAb. For solid phase method, 24 kDa protein, 76 kDa protein, NBW or DBW was previously fixed in a well of a cell culture plate. A method allowing anti-24 kDa protein MAb or 76 kDa protein MAb to the fixed antigens was used. Further, classes and subclasses of MAbs were determined according to Monoclonal mouse immunoglobulin isotyping kit (Pharmingen) as IgG1, IgG2a, IgG2b, IgG3, IgM, IgA, IgL (κ) and IgL (γ)

9) Biotinylation of MAbs

Purified MAbs were biotinylated to be provided to sandwich ELISA. By using 50 mM of carbonate buffer solution (pH 8.5), it was prepared to 20 mg/ml, 10 μl of NHS-biotin solution dissolved at 3 mg/100 μl in DMSO was added, and the mixture was stirred and then allowed to stand for 2 hours by icing. Subsequently, it was replaced with PBS, to 20 mg/ml.

1-2 Results

1) Characteristics, Classes and Subclasses of Anti-24 kDa Protein MAbs and 76 kDa Protein MAbs 5 types of MAbs having specificity against 24 kDa protein, and 4 types of MAbs having specificity against 76 kDa protein were obtained. Specificity against each solid phased antigens is shown in Tables 15 and 16.

TABLE 15

| MAbs | 24 kDa | NBW | DBW | Classes, subclasses, and types |
|---|---|---|---|---|
| 376 (PBW1) | + | − | + | IgG1 (κ) |
| 384 | + | − | + | IgG1 (κ) |
| 389 | + | − | + | IgG1 (κ) |

TABLE 15-continued

| MAbs | 24 kDa | NBW | DBW | Classes, subclasses, and types |
|---|---|---|---|---|
| 398 | + | − | + | IgG1 (κ) |
| 401 | + | − | + | IgG1 (κ) |

TABLE 16

| MAbs | 76 kDa | NBW | DBW | Classes, subclasses, and types |
|---|---|---|---|---|
| 505 (PBW2) | + | + | + | IgG1 (κ) |
| 506 (PBW3) | + | + | + | IgG1 (κ) |
| 504 | + | + | − | IgG1 (κ) |
| 512 | + | + | − | IgG1 (κ) |
| 501 | + | + | − | IgG1 (κ) |

2) Combination Conditions

Each MAb which showed a positive reaction against solid phased antigens was used as solid-phased or biotinylated antibodies, to select combinations of MAbs for detecting NBW and DBW from the view point of detection sensitivity in sandwich ELISA. As a result, as a combination for detecting NBW, a combination of plate fixed antibody PBW2 (FERM ABP-10273) with biotinylated antibody PBW3 (FERM ABP-10274) was selected. Further, as a combination for detecting DBW, a combination of plate fixed antibody PBW1 (FERM ABP-10272) with biotinylated antibody PBW2 was selected. The results of reactivity of PBW2 and PBW3 against various buckwheat crude proteins by sandwich ELISA are shown in Table 15. Further, the results of reactivity of PBW1 and PBW2 against various buckwheat crude proteins by sandwich ELISA are shown in Table 16.

3) Detection of NBW, DBW in a MAb Mixed System

Mabs selected by sandwich ELISA were mixed and the detection sensitivity of NBW and DBW was confirmed. In other words, for NBW, the case of using only PBW2 as plate fixed antibody was compared with the case of using a plate fixed antibody in which PBW1 and PBW2 are mixed, and a biotinylated PBW3 as secondary antibodies. Further, for DBW, the combination of a plate fixed antibody PBW1 with high detection sensitivity, with a biotinylated PBW2 was compared with the case of using a plate fixed antibody in which PBW1 and PBW2 are mixed, and a biotinylated PBW3 as secondary antibodies. As it is shown in FIGS. 17 and 18, it was revealed that the absorbance was higher for both NBW and DBW when plate antibodies were mixed, and that detection sensitivity could be increased.

2. Detection of NBW, DBW in Foods by Sandwich ELISA

With the combination of PBW1, PBW2 and PBW3 which was selected in the above 1., it was investigated whether buckwheat crude proteins could be detected from actual foods.

2-1 Materials and Methods

1) Preparation of Meat Product Models

Meat products were selected as food models for quantitative tests, and meat product models containing buckwheat crude proteins at each concentration were prepared with a composition shown in Table 17. Fat and muscle were removed from pork loin, and minced at 5 mm to be used as lean hog. According to each composition, additives were measured, mixed with a food processor, filled into a vinyl chloride tube and heated at 75° C. for 30 min.

TABLE 17

| Raw material | TEST 1 | TEST 2 | TEST 3 | Control |
|---|---|---|---|---|
| Lean hog (%) | 83.0 | 83.0 | 83.0 | 83.0 |
| NaCl(%) | 2.0 | 2.0 | 2.0 | 2.0 |
| Sodium Polyphate Na (%) | 0.2 | 0.2 | 0.2 | 0.2 |
| Sodium nitrite (ppm) | 120 | 120 | 120 | 120 |
| Sodium ascorbate (ppm) | 300 | 300 | 300 | 300 |
| water | 14.5 | 14.5 | 14.5 | 14.5 |
| Buckwheat crude protein (ppm) | 200 | 20 | 2 | 0 |
| Total (%) | 99.762 | 99.744 | 99.7422 | 99.742 |

2) Quantitative Analysis by Sandwich ELISA
(Salted Meat Model)

Each salted meat model was ground until being homogenized with a food processor, and used as a sample for analysis. 1 g of sample was measured and taken, 19 g of PBST was added, and the mixture was stirred for 30 sec with a homogenizer. The resultant was centrifuged at 3,000 rpm×20 min, and the supernatant was filtered with a filter. 0.5 ml of the filtrates was measured to which 9.5 ml of PBST was added and used as a sample for ELISA. For a detection line, serial dilution of buckwheat crude protein using similarly PBST was used.

(Heated Product Model)

Each heated product model was ground until being homologous with a food processor, and used as a sample for analysis. 1 g of sample was measured and taken, 19 g of PBS containing 1% SDS and 1% 2-mercaptoethanol was added, and the mixture was stirred for 30 sec with a homogenizer. Subsequently, a heating treatment was performed at 100° C. for 1 hour. After cooling, centrifugation was performed at 3,000 rpm for 20 min, and the supernatant was filtered with a filter. 0.5 ml of the filtrates was measured to which 9.5 ml of PBST was added, and used as a sample for ELISA. For detection line, serial dilution of buckwheat crude protein which has been similarly treated with SDS and 2-mercaptoethanol was treatment was used.

For the analysis of buckwheat crude protein in meat product model by sandwich ELISA, the results of salted meat models are shown in Table 18, and the results of heat product models are shown in Table 19.

TABLE 18

| | TEST 1 | TEST 2 | TEST 3 | Control |
|---|---|---|---|---|
| Added amount (ppm) | 200.0 | 20.0 | 2.0 | 0.0 |
| Assay value (ppm) | 189.3 | 16.2 | 1.8 | N.D. *2 |
| Yield (%) *1 | 94.6% | 81.0% | 90.5% | — |

*1: (assay value/added amount) × 100
*2: not detected

TABLE 19

| | TEST 1 | TEST 2 | TEST 3 | Control |
|---|---|---|---|---|
| Added amount (ppm) | 200.0 | 20.0 | 2.0 | 0.0 |
| Assay value (ppm) | 156.6 | 18.0 | 2.6 | N.D. |
| Yield (%) *1 | 78.3% | 90.0% | 133% | — |

*1: (assay value/added amount) × 100
*2: not detected

From the above results, buckwheat crude protein was detectable in a high yield, even when it is a buckwheat crude protein which is non-heated such as a salted meat model, or a buckwheat crude protein which has been heat-denatured such as a heated product model. From these results, it was revealed that buckwheat in any state can be analyzed with a high sensitivity, regardless of whether it is non-heated (native) or heated (denatured), by combining MAbs bondable to native buckwheat proteins and MAbs bondable to denatured buckwheat crude proteins.

3. Detection of Denatured/Native Buckwheat Crude Proteins by Immunochromatography
3-1 Materials and Methods
1) Preparation of Gold Colloid Labeled and Conjugate Pads PBW3MAb solutiton was prepared to 1 mg/ml with 2 mM of borate buffer solution (pH 9.0). 500 µl of MAb solution was added to 5 ml of gold colloid solution (Sigma) which was previously prepared to pH 9.0 with 0.2 M carbonic potassium solution, and after allowing to react at room temperature for 30 min, 625 µl of 10% BSA solution was added and was further allowed to react for 15 min. Centrifugation was performed and it was prepared to OD525=1.0 with 1% BSA solution. The resultant was applied to a glass wool conjugate pad (Nihon Millepore) to 68 µl/cm², and dried.

2) Preparation of Antibody Fixed Membranes

MAb solution of PBW1 and PBW2 was prepared to 8 mg/ml in PBS, mixed at a ratio of 1:1. The resultant was applied linearly on a nitrocellulose membrane and dried. Then, the resultant was blocked for 1 hour, at 37° C. with 10 mM phosphate buffer (pH 7.5) containing 1% skim milk, washed with 10 mM phosphate buffer (pH 7.5), and dried.

3) Construction and Estimation of Immunochromato Strips

A sample pad, a conjugate pad, an antibody-fixed membrane and an absorption pad prepared in the above were applied respectively, to make an immunochromato strip. Meat product models prepared in the above were diluted appropriately and used as a test solution.

3-2 Results

With the combination of membrane-applied MAbs, PBW1+PBW2, with gold-colloid labeled MAb PBW3, buckwheat protein could be detected up to 50 ppb (2 ppm in foods) regardless of whether it is heated or non-heated. From these results, it was revealed that immunochromato stip that can respond to any case can be constructed, even when a buckwheat protein which has been contaminated during the manufacture process is the target, or when a product after heating is the target.

When PBS containing 0.01 M of urea +0.2% 2-mercaptoethanol as a blank was dropped to a commercial immunochromato strip to detect allergens, a non-specific band appeared, and it was tested as false positive. Thus, a protein denaturant to detect effectively allergens from food protein denatured by heating and the like, could not be used, and there was a possible risk that subjects detectable as allergens would be limited to a very narrow range.

EXAMPLE 5

1. Establishment of Anti-Ara h1MAbs
1-1 Materials and Methods 5-fold amount of 20 mM bis-tris-propane buffer (pH 7.2) was added to commercial raw peanuts. The mixture was stirred for 2 h at room temperature, centrifuged at 3000×g, and the precipitates and oil content were removed. The obtained water-soluble fractions were further centrifuged at 1000×g, to obtain supernatants. The supernatants were further purified by using Source Q (Amsharm Pharmacia) with 20 mM bis-tris-propane buffer (pH 7.2) and linear gradient of NaCl (0-1 M). The purified Ara h1 fractions were dialyzed with distilled water, lyophilized, and used as denatured Ara h1 (hereinafter referred to as NAh1). Further, for denatured Ara h1 (hereinafter referred to as DAh1), 10 mg of NAh1 was measured, 6 g of urea, 0.2 ml of 2-mercaptoethanol (hereinafter referred to as 2-ME), 1 ml of 50 mM of Tris-HCl buffer solution (pH 8.6) and 1.5 ml of distilled water were added. The resultant was covered with an aluminum cap, which was heated at 100° C. in an oil bath to perform denaturation treatment. Subsequently, dialysis was performed followed by lyophilization. 0.1% NAh1 solution and 0.1% DAh1 solution were prepared by using these lyophilizates with saline and aliquoted at 500 µl into 1 ml-volume Eppendorf tubes, to make an antigen solution. The solution was store by freezing at −20° C. until immunization.

2) Immunization

As test animals, 5 BALB/c mice (CLEA Japan) of 5 weeks-old were used. For the primary immunization, an emulsion prepared by adding a complete Freund's adjuvant (Difco) to an Eppendorf tube each filled with 500 µl of 0.1% NAh1 solution and 0.1% DAh1 solution at an equal amount, and stirring in a vortex mixer was used. The emulsion was injected intraperitoneally in an amount of 150 µl per mouse. Further, additional immunizations were performed twice at 3 weeks interval. For immunization, an emulsion prepared by adding an incomplete Freund's adjuvant (Difco) to Eppendorf tubes each filled with 500 µl of 0.1% NAh1 solution and 0.1% DAh1 solution at an equal amount, and stirring in a vortex mixer was used. The emulsion was injected intraperitoneally in an amount of 150 µl per mouse.

3) Measurement of Antibody Titer in Blood

One week after injecting NAh1 solution or DAh solution as the primary or additional immunization, blood was collected from tail vein of each BALB/c mouse. The blood collected was allowed to stand for 2 hours at room temperature, centrifuged to obtain serum. 10-fold serial dilution of these sera was prepared, and the anti-NAh1 antibody titer and anti-DAh1 antibody titer in mouse blood were examined by non-competitive ELISA. Meanwhile, alkaline phosphatase labeled-anti mouse IgG (H+L) antibodies (Jackson ImmunoResearch Laboratories Inc.) were used as secondary antibodies.

4) Preparation of Hybridomas

Hybridomas were prepared according to the method of Keller and Milstein (1975). In other words, 100 µl of 0.1% NAh1 solution and 0.1% DAh1 solution were injected to tail-vein to a mouse whose antibody titer has sufficiently increased. Spleen was extracted from the mouse 4 days later, axenically. Spleen was extracted axenically from the mouse 4 days after intravenous injection. The spleen was chopped, subsequently washed with RPMI 1640, allowed to pass through a sterilized nylon mesh (Cell Strainer, 70 mm, Becton Dickinson), to obtain a spleen cell suspension. Spleen cells were harvested by a centrifugation at 1,000 rpm×10 min, and the cells were counted after resuspending in RPMI 1640. The spleen cell suspension and mouse myeloma cells (P3X63Ag8.653) were mixed such that the cell count becomes 10:1, and then centrifuged again at 1,000 rpm×10 min to obtain a pellet. 45% polyethylene glycol with a mean molecular weight of 3,350 was dropped to the pellet to allow a cell fusion. RPMI 1640 was added to the cell solution, which was diluted. A pellet was obtained by centrifugation. A HAT selective medium in which 100 µM of hypoxanthine, 0.4 µM of aminopterin and 16 µM of thymidine was added to a medium for hybridoma (RPMI1640 medium containing 10% bovine fetal serum, 40 mM of 2-mercaptoethanol, 100 U/ml of penicillin, 100 mg/ml of streptomycin) was added to the pellet. The resultant was aliquoted in 24-well cell culture plate (Becton Dickinson) to $5\times10^6$ cells/well, and was cultured at 37° C., in the presence of 5% $CO_2$.

5) Cloning by Limiting Dilution

Presence of hybridomas provided as primary antibodies for ELISA and producing NAh1 or DAh1 was examined in the culture supernatant of each well of cell culture plate. Hybridomas which tested positive against NAh1 or DAh1 by ELISA were transferred to a 96-well cell culture plate (Becton Dickinson) and cloned by limiting dilution to 0.9 cell/well. Meanwhile, as feeder cells, thymocytes of 4-weeks old BALB/c mouse were added to each well of the 96-well cell culture plate, to $5\times10^6$ cells/well. RPMI 1640 media containing 10% of bovine fetal serum, 40 mM of 2-mercaptoethanol, 100 U/ml of penicillin, 100 µg/ml of streptomycin were used for culturing cloned hybridomas.

6) Screening of Antibodies

To screen monoclonal antibodies, clones of different specificities were obtained by examining the difference of reactivity against 4 types, that is NAh1, DAh1, or native substances of peanut crude protein (hereinafter referred to as NP-e) and urea-treated (hereinafter referred to as DP-e). Further, for NP-e, 5-fold amount of 20 mM bis-tris-propane buffer (pH 7.2) to peanuts, the mixture was stirred for 2 hours at room temperature and centrifuged twice. Subsequently, the obtained supernatants were dialyzed and lyophilized. Further, for DP-e, 10 mg of NP-e was measured, 6 g of urea, 0.2 ml of 2-ME, 1 ml of 50 mM Tris-HCl buffer solution (pH 8.6) and 1.5 ml of distilled water were added. The resultant was covered with an aluminum cap, and heated at 100° C. for 1 hour in an oil bath to perform a denaturation treatment. Reactivity against NAh1, NP-e, DAh1 or DP-e in the supernatant was investigated by non-competitive ELISA.

7) 7) Collection of Ascitic Fluid and Purification of MAb

According to Jones et al. (1990), 0.2 ml of incomplete Freund's adjuvant was injected to a BALB/c mouse intraperitoneally. One week after, $5\times10^6$ cells/well of cloned hybridomas per mouse were inoculated. After accumulation of ascitic fluid, fluid was collected with a syringe. The collected ascitic fluid was purified by Protein G column (Amersham pharmacia).

8) Characteristics of MAbs; Classes, Subclasses and Types of MAbs

Solid phase method was used to determine the characteristics of anti-NAh1 MAbs or anti-DAh1 MAbs. As a solid phase method, a method comprising the steps of fixing NAh1, DAh1, NP-e or DP-e were previously in wells of cell culture plate and to allowing anti-NAh1 MAbs or DAh1 MAbs to these fixed antigens was used. Further, classes and subclasses of MAbs were determined according to Monoclonal mouse immunoglobulin isotyping kit (Pharmingen) as IgG1, IgG2a, IgG2b, IgG3, IgM, IgA, IgL (κ) and IgL (γ).

9) Biotinylation of MAbs

Purified MAbs were biotinylated to be provided to sandwich ELISA. By using 50 mM of carbonate buffer solution (pH 8.5), it was prepared to 20 mg/ml, 10 µl of NHS-biotin solution dissolved at 3 mg/100 ml in DMSO was added, and the mixture was stirred and then allowed to stand for 2 hours by icing. Subsequently, it was replaced with PBS, to 20 mg/ml.

1-2 Results

1) Characteristics, Classes and Subclasses of Anti-NAh1 MAbs and DAh1 MAbs

7 MAbs having specificity against NAh1, and 3 MAbs having specificity against DAh1 were obtained. Specificity against each solid phased antigen is shown in Tables 20 and 21.

TABLE 20

| MAbs | NAh 1 | DAh 1 | NP-e | DP-e | Classes, subclasses, and types |
|---|---|---|---|---|---|
| 203 | +* | − | + | − | IgG1 (κ) |
| 217 (PAh1 - 1) | + | − | + | − | IgG1 (κ) |
| 223 | + | − | + | − | IgG1 (κ) |
| 236 (PAh1 - 2) | + | + | + | + | IgG1 (κ) |
| 427 | + | − | + | − | IgG1 (κ) |
| 432 | + | + | + | + | IgG1 (κ) |
| 451 | + | + | + | + | IgG1 (κ) |

TABLE 21

| MAbs | NAh 1 | DAh 1 | NP-e | DP-e | Classes, subclasses, and types |
|---|---|---|---|---|---|
| 967 | −* | + | − | + | IgG1 (κ) |
| 970 | − | + | − | + | IgG3 (κ) |
| 971 (PAh1 - 3) | − | + | − | + | IgG1 (κ) |

2) Combination Conditions

Each MAb which showed a positive reaction against solid phased antigen was used as solid-phased or biotinylated antibodies, to select combinations of MAbs for detecting NP-e and DP-e from the view point of detection sensitivity in sandwich ELISA. As a result, as a combination for detecting NP-e, a combination of plate fixed antibody PAh1-2 (FERM ABP-10270) with biotinylated antibody PAh1-1 (FERM ABP-10269) was selected. Further, as a combination for detecting DP-e, a combination of plate fixed antibody PAh-2 with biotinylated antibody PAh 1-3 (FERM ABP-10271) was selected (FIGS. 19 and 20).

3) Detection of NP-e and DP-e in a MAb Mixed System

PAh1-2 (cell deposit number) to solid phase, PAh1-1 (cell deposit number) for biotinilyation and PAh1-3 (cell deposit number) were mixed to confirm the detection sensitivity of NP-e and DP-e. Each MAb concentration was set to 50 μg/ml. As a result, both NP-e and DP-e were detectable in a MAb mixed system (FIGS. 21 and 22).

2. Detection of Peanut Crude Proteins in Foods by Sandwich ELISA

With the combination of PAh1-1, PAh1-2 and PAh1-3 selected in the above 1., it was investigated whether peanut crude proteins in actual foods could be detected.

2-1 Materials and Methods

1) Preparation of Meat Product Models

Meat products were selected as food models for quantitative test, and meat product models containing peanut crude proteins at each concentration were prepared with a composition shown in Table 22. Fat and muscle were removed from pork loin, and minced at 5 mm to be used as lean hog. According to each composition, additives were measured, mixed with a food processor, filled into a vinyl chloride tube and heated at 75° C. for 30 min.

TABLE 22

| Raw material | TEST 1 | TEST 2 | TEST 3 | Control |
|---|---|---|---|---|
| Lean hog (%) | 83.0 | 83.0 | 83.0 | 83.0 |
| NaCl (%) | 2.0 | 2.0 | 2.0 | 2.0 |
| Sodium polyphosphate (%) | 0.2 | 0.2 | 0.2 | 0.2 |
| Sodium nitrite (ppm) | 120 | 120 | 120 | 120 |
| Sodium ascorbate (ppm) | 300 | 300 | 300 | 300 |

TABLE 22-continued

| Raw material | TEST 1 | TEST 2 | TEST 3 | Control |
|---|---|---|---|---|
| water | 14.5 | 14.5 | 14.5 | 14.5 |
| Sodium casein (ppm) | 200 | 20 | 2 | 0 |
| Total (%) | 99.762 | 99.744 | 99.7422 | 99.742 |

2) Quantitative Analysis by Sandwich ELISA (Salted Meat Model)

Each salted meat model was ground with a food processor until being homologous, and used as a sample for analysis. 1 g of sample was measured and taken, 19 g of PBST was added, and the mixture was stirred for 30 sec with a homogenizer. The resultant was centrifuged at 3000 rpm×20 min, and the supernatant was filtered with a filter. 0.5 ml of the filtrates was measured, 9.5 ml of PBST was added and used as a sample for ELISA. For a detection line, serial dilution of peanut crude protein using similarly PBST was used.

(Heated Product Model)

Each heated product model was ground until being homologous with a food processor, and used as a sample for analysis. 1 g of sample was measured and taken, 19 g of PBS containing 1M of urea and 0.1% 2-ME was added, and the mixture was stirred for 30 sec with a homogenizer. Subsequently, a heating treatment was performed at 100° C. for 1 hour. After cooling, centrifugation was performed at 3,000 rpm for 20 min, and the supernatant was filtered with a filter. 0.5 ml of the filtrates was measured, 9.5 ml of PBST was added, and used as a sample for ELISA. For detection line, serial dilution of peanut crude protein which has been similarly treated with 1M urea and 0.1% 2-ME was used. Further, by using PBST it was extracted from sample for analysis, and was compared with when peanut crude protein dissolved in PBST was used as a detection line, and not using urea and 2-ME.

2-2 Results

The analysis results of peanut crude proteins in meat product models by sandwich ELISA are shown in Table 23 for salted meat models, in Table 24 for heated product models, and in Table 25 for those which have been extracted only with PBST.

TABLE 23

|  | TEST 1 | TEST 2 | TEST 3 | Control |
|---|---|---|---|---|
| Added amount (ppm) | 200.0 | 20.0 | 2.0 | 0.0 |
| Assay value (ppm) | 206.0 | 18.4 | 1.8 | N.D. *2 |
| Yield (%) *1 | 103.0 | 92.0 | 90.0 | — |

*1: (assay value/added amount) × 100
*2: not detected

TABLE 24

|  | TEST 1 | TEST 2 | TEST 3 | Control |
|---|---|---|---|---|
| Added amount (ppm) | 200.0 | 20.0 | 2.0 | 0.0 |
| Assay value (ppm) | 137.0 | 19.5 | 10.3 | N.D. *2 |
| Yield (%) *1 | 68.5 | 97.5 | 515.0 | — |

*1: (assay value/added amount) × 100
*2: not detected

TABLE 25

|  | TEST 1 | TEST 2 | TEST 3 | Control |
|---|---|---|---|---|
| Added amount (ppm) | 200.0 | 20.0 | 2.0 | 0.0 |
| Assay value (ppm) | N.D. *2 | N.D. | N.D. | N.D. |
| Yield (%) *1 | — | — | — | — |

From the above results, peanut protein was detectable in a high yield, even when it is a peanut crude protein which is not heated such as a salted meat model, or a peanut crude protein which has been heat-denatured such as a heated product model. From these results, it was revealed that peanut can be analyzed with a high sensitivity, regardless of whether it is non-heated (native) or heated (denatured), by combining MAbs bondable to native peanut proteins and MAbs bondable to denatured peanut crude proteins. Further, it was revealed that it was effective to use urea and 2-ME for extracting peanut crude proteins from foods, and that it is necessary to be bondable to Ah1 which has been denatured with urea.

3. Detection of Denatured/Native Peanut Crude Protein by Immunochromatography 3-1 Materials and Methods 1) Preparation of Gold Colloid Labeled and Conjugate Pads MAb solution of PAh1-1 and PAh 1-3 was prepared to 1 mg/ml with 2 mM of borate buffer solution (pH 9.0). 500 ml of MAb solution was added to 5 ml of gold colloid solution (Sigma) which was previously prepared to pH 9.0 with 0.2 M carbonic potassium solution, and after allowing to react at room temperature for 30 min, 625 µl of 10% BSA solution was added and was further allowed to react for 15 min. Centrifugation was performed and it was prepared to OD525=2.0 with 1% BSA solution, at a ratio of 1:1. The resultant was applied to a glass wool conjugate pad to 68 µl/cm², and dried.

2) Preparation of Antibody Fixed Membranes

MAb solution of PAh 1-2 was prepared to 4 mg/ml in PBS. The resultant was applied linearly on a nitrocellulose membrane, and dried. Then, the resultant was blocked for 1 hour at 37° C. with 10 M phosphate buffer (pH 7.5) containing 1% skim milk, washed with 10 mM phosphate buffer (pH 7.5) and dried.

3) Construction and Estimation of Immunochromato Strips

A sample pad, a conjugate pad, an antibody-fixed membrane and an absorption pad prepared in the above were applied respectively, to make an immunochromato strip. Meat product models prepared in the above 2. were diluted appropriately and used as a test solution.

3-2 Results

With the combination of membrane-applied MAb PAh1-1, with gold-colloid labeled MAbs PAh1-1 and PAh1-3, peanut crude proteins could be detected up to 50 ppb (2 ppm in foods) regardless of whether it is heated or non-heated. From these results, it was revealed that immunochromato stip that can respond to any case can be constructed, when a peanut protein which has been contaminated during the manufacture process is the target, or when a product after heating is the target.

When PBS containing 0.01 M of urea and 0.2% 2-ME as a blank was dropped to a commercial immunochromato strip to detect allergens, a non-specific band appeared, and it was tested as false positive. Thus, a protein denaturant to detect effectively allergens from food protein denatured by heating and the like, could not be used, and it was estimated with fear that subjects detectable as allergen would be limited within a very narrow range.

INDUSTRIAL APPLICABILITY

According to the present invention, in a immunological method for detecting milk allergens, albumen allergens, flour allergens, buckwheat allergens and peanut allergens contained in foods, these allergens can be detected accurately, quantitatively and qualitatively regardless of whether it is denatured/native.

The invention claimed is:

1. A method for detecting albumen allergens in a sample by sandwich ELISA, which method comprises the following steps (a) to (c):
   (a) preparing an immune complex by allowing an albumen allergen in the sample to contact a first anti-native ovalbumin monoclonal antibody recognizing a native ovalbumin, bound to an insolubilized carrier, and a first anti-reduced carboxymethylated ovalbumin monoclonal antibody recognizing a denatured ovalbumin, bound to the same insolubilized carrier;
   (b) preparing a labeled immune complex by allowing the immune complex prepared in step (a) to contact a labeled second anti-native ovalbumin monoclonal antibody recognizing a native ovalbumin and a labeled second anti-reduced carboxymethylated ovalbumin monoclonal antibody recognizing a denatured ovalbumin, wherein the second monoclonal antibody recognizing a native ovalbumin recognizes a different epitope of native ovalbumin than the epitope recognized by the first monoclonal antibody recognizing a native ovalbumin, and the second monoclonal antibody recognizing a denatured ovalbumin recognizes a different epitope of denatured ovalbumin than the epitope recognized by the first monoclonal antibody recognizing denatured ovalbumin; and
   (c) detecting native and denatured albumen allergen in the sample by detecting the labeled immune complex prepared in step (b).

2. The method for detecting albumen allergens according to claim 1, wherein
   the anti-ovalbumin monoclonal antibodies recognizing a native ovalbumin are the anti-ovalbumin monoclonal antibody PNOA1 produced by the hybridoma of Accession No: FERM BP-10265 and the anti-ovalbumin monoclonal antibody PNOA2 produced by the hybridoma of Accession No: FERM BP-10266; and
   the anti-ovalbumin monoclonal antibodies recognizing a reduced carboxymethylated ovalbumin are the anti-ovalbumin monoclonal antibody PDOA1 produced by the hybridoma of Accession No: FERM BP-10275 and the anti-ovalbumin monoclonal antibody PDOA2 produced by the hybridoma of Accession No: FERM BP-10276.

3. A method for detecting albumen allergens in a sample by immunochromatography, which method comprises the following steps (a) to (c):
   (a) preparing an antigen-antibody complex by allowing an albumen allergen in the sample to contact a first anti-native ovalbumin monoclonal antibody recognizing a native ovalbumin and a first anti-reduced carboxymethylated ovalbumin monoclonal antibody recognizing a denatured ovalbumin, wherein each of the first monoclonal antibodies is labeled with gold colloid;
   (b) allowing the antigen-antibody complex to move on a test strip by capillary action; and
   (c) detecting native and denatured albumen allergen in the sample by the presence or absence of a colored line appearing on the test strip by a trapping of the antigen-antibody complex by a second anti-native ovalbumin monoclonal antibody recognizing a native ovalbumin and a second anti-reduced carboxymethylated ovalbumin monoclonal antibody recognizing a denatured ovalbumin, wherein the second monoclonal antibody recognizing a native ovalbumin recognizes a different epitope of native ovalbumin than the epitope recognized by the first monoclonal antibody recognizing a native ovalbumin, and the second monoclonal antibody recognizing a denatured ovalbumin recognizes a different epitope of denatured ovalbumin than the epitope recognized by the first monoclonal antibody recognizing denatured ovalbumin, and the second monoclonal antibodies are fixed in advance at a given position on the test strip.

4. The method for detecting albumen allergens according to claim 3, wherein
   the anti-ovalbumin monoclonal antibodies recognizing a native ovalbumin are the anti-ovalbumin monoclonal antibody PNOA1 produced by the hybridoma of Accession No: FERM BP-10265 and the anti-ovalbumin monoclonal antibody PNOA2 produced by the hybridoma of Accession No: FERM BP-10266; and
   the anti-ovalbumin monoclonal antibodies recognizing a reduced carboxymethylated ovalbumin are the anti-ovalbumin monoclonal antibody PDOA1 produced by the hybridoma of Accession No: FERM BP-10275 and the anti-ovalbumin monoclonal antibody PDOA2 produced by the hybridoma of Accession No: FERM BP-10276.

* * * * *